United States Patent
Ghosh et al.

(10) Patent No.: US 10,875,836 B2
(45) Date of Patent: Dec. 29, 2020

(54) CALLYSPONGIOLIDE, ANALOGS THEREOF AND USES THEREOF

(71) Applicant: Purdue Research Foundation, West Lafayette, IN (US)

(72) Inventors: Arun K. Ghosh, West Lafayette, IN (US); Luke A. Kassekert, Lino Lakes, MN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/304,652

(22) PCT Filed: May 26, 2017

(86) PCT No.: PCT/US2017/034760
§ 371 (c)(1),
(2) Date: Nov. 26, 2018

(87) PCT Pub. No.: WO2017/205791
PCT Pub. Date: Nov. 30, 2017

(65) Prior Publication Data
US 2019/0218198 A1      Jul. 18, 2019

Related U.S. Application Data

(60) Provisional application No. 62/342,601, filed on May 27, 2016.

(51) Int. Cl.
*A61P 35/00* (2006.01)
*C07D 313/00* (2006.01)
*A61K 31/436* (2006.01)

(52) U.S. Cl.
CPC .......... *C07D 313/00* (2013.01); *A61K 31/436* (2013.01)

(58) Field of Classification Search
CPC ....................................................... A61P 35/00
See application file for complete search history.

(56) References Cited

FOREIGN PATENT DOCUMENTS

| CN | 109195666 A | 1/2019 |
|---|---|---|
| WO | WO-2017205791 A1 | 11/2017 |

OTHER PUBLICATIONS

Han, H. "Targeted Prodrug Design to Optimize Drug Delivery." AAPS Pharmsci. (2000), vol. 2 (1) article 6, pp. 1-11. (Year: 2000).*
Ettmayer, P., et al. "Lessons Learned from Marketed and Investigational Prodrugs." J. Med. Chem. (2004) 47(10), pp. 2393-2404. (Year: 2004).*
Testa, B. "Prodrug research: futile or fertile?" Biochem. Pharm. (2004) 68, pp. 2097-2106. (Year: 2004).*
Zhou, J., et al. "Total Synthesis and Stereochemical Assignment of Callyspongiolide." J. Am. Chem. Soc. (2016), vol. 138, pp. 6948-6951. (Year: 2016).*
Pham, Cong-Dat, et al. "Callyspongiolide, a Cytotoxic Macrolide from the Marine Sponge *Callyspongia* sp." Org. Lett. (2014), vol. 16, pp. 266-269. (Year: 2014).*
U.S. Appl. No. 62/342,601, filed May 27, 2016, Callyspongiolide, Analogs Thereof and Uses Thereof.
PCT/US2017/034760, May 26, 2017, Callyspongiolide, Analogs Thereof and Uses Thereof.
"International Application Serial No. PCT/US2017/034760, International Search Report dated Oct. 10, 2017", 2 pgs.
"International Application Serial No. PCT/US2017/034760, Written Opinion dated Oct. 10, 2017", 4 pgs.
Pham, et al., "Callyspongiolide a Cytotoxic Macrolide from the Marine Sponge *Callyspongia* sp", Org Lett vol. 16(1), (2014), 266-269.
Zhou, et al., "Total Synthesis and Stereochemical Assignment of Callyspongiolid", J. Am. Chem. Soc. vol. 138 entire document, (May 26, 2016), 6948-6951.
"European Application Serial No. 17803698.4, Office Action dated Jan. 11, 2019", 3 pgs.
"International Application Serial No. PCT/US2017/034760, International Preliminary Report on Patentability dated Dec. 6, 2018", 6 pgs.
"European Application Serial No. 17803698.4, Extended European Search Report dated Oct. 29, 2019", 5 pgs.

* cited by examiner

*Primary Examiner* — John S Kenyon
(74) *Attorney, Agent, or Firm* — Schwegman Lundberg & Woessner, P.A.

(57) ABSTRACT

Described herein are compounds of the formula (I)-(III) (or a pharmaceutically acceptable salt, polymorph, prodrug, solvate or clathrate thereof), as well as methods of making and using compounds of the formula (I)-(III) to, among other things, treat various forms of cancer.

15 Claims, No Drawings

CALLYSPONGIOLIDE, ANALOGS THEREOF AND USES THEREOF

CROSS-REFERENCE TO RELATED APPLICATIONS

This application is a U.S. National Stage Filing under 35 U.S.C. § 371 from International Application No. PCT/US2017/034760, filed May 26, 2017, and published as WO 2017/205791 A1 on Nov. 30, 2017, which claims the benefit of U.S. Provisional Application Ser. No. 62/342,601, filed May 27, 2016, the entirety of which applications is incorporated by reference as if fully set forth herein.

BACKGROUND OF THE INVENTION

Marine sponges of the genus *Callyspongia* have proven to be rich sources of natural products that display cytotoxic activity. Examples of such natural products include cally-azepin (a nitrogenous macrocycle displaying moderate cytotoxicity against K562 and A549 cell lines) and a methanolic extract of the sponge *Callyspongia* sp. (observed complete inhibition of the murine lymphoma cell line L5178Y). In addition, testing of callyspongiolide against human Jurkat J16 T and Ramos B lymphocytes revealed $IC_{50}$ values of 70 and 60 nM, respectively.

DETAILED DESCRIPTION OF THE INVENTION

In the continuing interest of synthesizing bioactive natural products, and taking into consideration the novel structure of the callyspongiolide macrolide, the inventors sought to establish a convergent and enantioselective synthesis of callyspongiolide to aid in structural determination and to further probe biological studies of not only callyspongiolide, but also analogs of the compound.

Reference will now be made in detail to certain examples of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Various examples described herein are directed to a compound of the formula (I) and (II), or a pharmaceutically acceptable salt, polymorph, prodrug, solvate or clathrate thereof, as well as methods of making and using compounds of the formula (I) and/or (II) to, among other things, treat various forms of cancer (e.g., chronic myelogenous leukemia, lung carcinoma, lymphoma, T-acute lymphoblastic leukemia, and Burkitt's lymphoma):

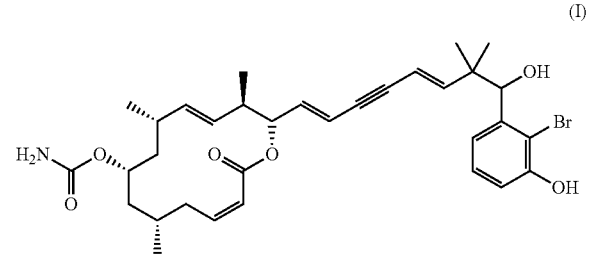

(I)

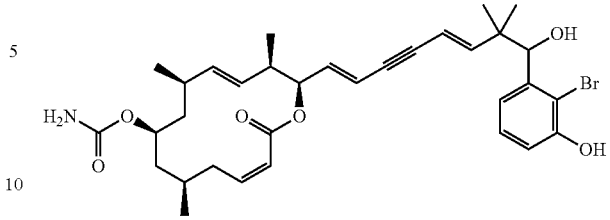

(II)

Various other examples described herein are directed to a compound of the formula (III), or a pharmaceutically acceptable salt, polymorph, prodrug, solvate or clathrate thereof, as well as methods of making and using compounds of the formula (III) to, among other things, treat various forms of cancer:

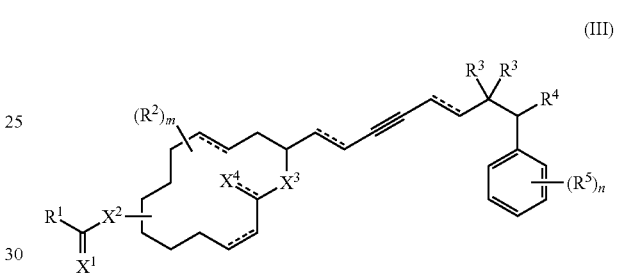

(III)

wherein:
each dashed bond independently represents a single or a double bond and, when a dashed bond represents a double bond, the double bond can have the E- or Z-configuration;
$R^1$ is H, alkyl, $R^2$—$(CH_2)_q$—$X^3$—, $R^2$—$(CH_2)_q$—$C(O)NR^6$$(CH_2)_q$—$X^3$—, $OR^6$ or $N(R^6)_2$, wherein each $R^6$ independently represents H, alkyl, aryl, alkaryl, or arylalkyl and each q is, independently an integer from 0 to 9;
$X^1$ is O, $NR^6$ or S;
$X^2$ is O, $NR^6$ or S;
each $R^2$ is, independently, H, halo, alkyl, aryl, alkaryl, arylalkyl, heterocyclyl, $OR^6$, $S(O)_pR^6$ or $N(R^6)_2$, wherein p is an integer from 0 to 2 and m is an integer from 1 to 10 (e.g., m is 1-5, 2-5, 3-5 or 3 to 7 and/or n is 2; in some examples m is 3 and/or n is 2);
$X^3$ is O, $NR^6$, $S(O)_p$ or $C(R^6)_2$;
$X^4$ is O, $NR^6$ or S or $X^4$ is $R^2$ when there is a single bond between $X^4$ and the carbon atom to which $X^4$ is bound;
each $R^3$ is, independently, H, halo, alkyl, aryl, alkaryl, arylalkyl, heterocyclyl, $OR^6$, $S(O)_pR^6$ or $N(R^6)_2$;
$R^4$ is H, halo, alkyl, aryl, alkaryl, arylalkyl, heterocyclyl, $OR^6$, $S(O)_pR^6$, $N(R^6)_2$ or $X^1C(O)(CH)_qR^6$;
each $R^5$ is, independently, H, halo, alkyl, aryl, alkaryl, arylalkyl, heterocyclyl, $OR^6$, $S(O)_pR^6$ or $N(R^6)_2$, wherein n is an integer from 0 to 4;
or a pharmaceutically acceptable salt, polymorph, prodrug, solvate or clathrate thereof.

In some examples, the compound of the formula (III) is not a compound of the formula (I) and/or (II). Also contemplated herein are antibodies conjugated to compounds of the formula (III) via any suitable point in the molecule (e.g., via an ether, ester or amide bond).

In some examples, the compound of the formula (III) is a compound of the formula:

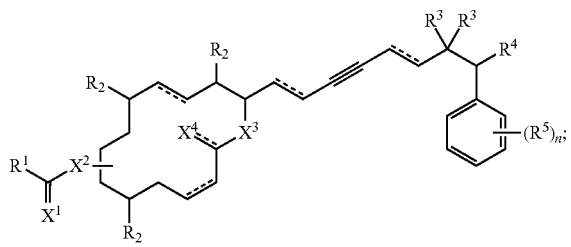

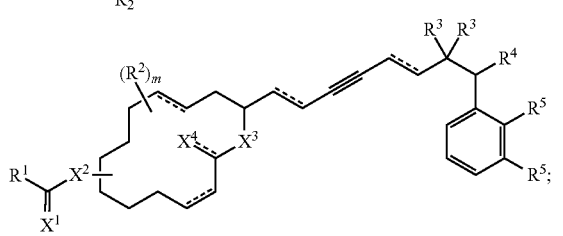

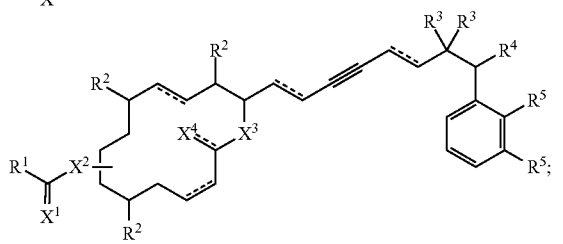

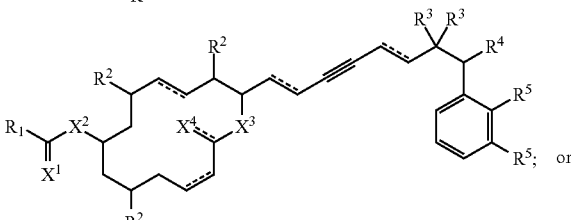

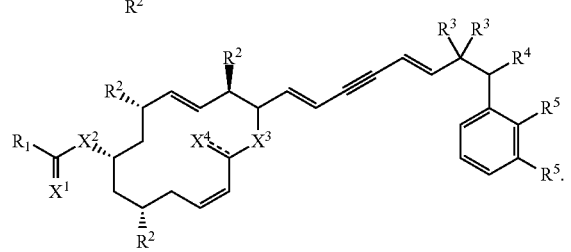

In some examples, $X^1$, $X^2$, $X^3$ and $X^4$ are each O. In other examples, each dashed bond represents a double bond in the configuration shown in the compound of the formula (III). In still other examples, $R^1$ is $N(R^6)_2$, wherein each $R^6$ independently represents H, alkyl, aryl, alkaryl, or arylalkyl. In other examples, $R^1$ is the group $R^2$—$(CH_2)_q$—$X^3$— or $R^2$—$(CH_2)_q$—$C(O)NR^6(CH_2)_q$—$X^3$—, wherein each q is, independently an integer from 0 to 9 (e.g., 1 to 9, 1 to 8, 0 to 5, and 0 to 8). One example of the group $R^2$—$(CH_2)_q$—$X^3$— includes the group heterocyclyl-$(CH_2)_q$—$X^3$— (wherein q is, independently an integer from 0 to 9), such as the group wherein the wavy line is the point at which $R^1$ attaches to the carbon atom bearing the $X^1$ group:

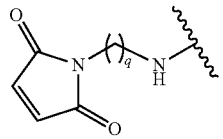

$q = 1-9$

One example of the group $R^2$—$(CH_2)_q$—$C(O)NR^6(CH_2)_q$—$X^3$— includes the group heterocyclyl-$(CH_2)_q$—$C(O)NR^6(CH_2)_q$—$X^3$— (wherein each q is, independently an integer from 0 to 9), such as the group:

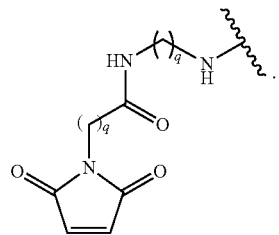

In some examples, each $R^2$ is, independently, $C_1$-$C_6$ alkyl (e.g., methyl, ethyl or propyl). In other examples, each $R^5$ is, independently, halo or $OR^6$. In still other examples, each $R^3$ is, independently, $C_1$-$C_6$ alkyl. And in other examples, $R^4$ is $OR^6$. In still other examples, $R^4$ is $X^1C(O)(CH)_qR^6$. An example of the group $X^1C(O)(CH)_qR^6$ includes —NH—C(O)—$(CH_2)_q$—$R^6$ (wherein q is, independently an integer from 0 to 9), wherein $R^6$ is:

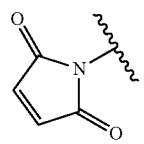

In some examples, the compounds of the formula (III) can be synthesized by the method comprising:

contacting (e.g., reacting) a compound of the formula (IV):

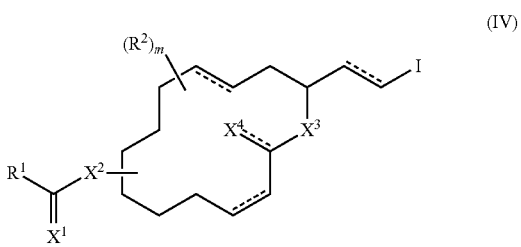

(IV)

with a compound of the formula (V):

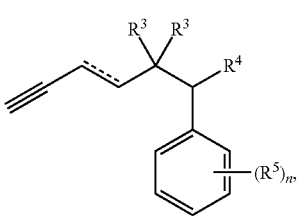

(V)

wherein the substituents $R^1$-$R^6$ and $X^1$—$X^4$ are defined herein.

In some examples, the compound of the formula (IV) and (V) can be synthesized from a compound of the formula (VI) and (VII), respectively:

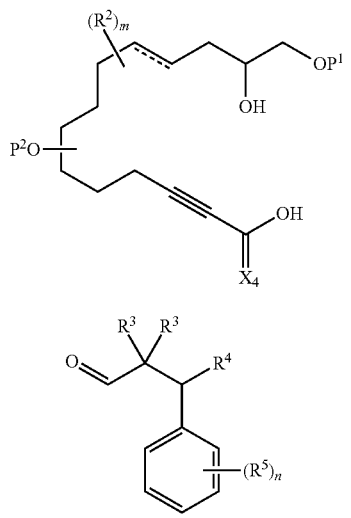

(VI)

(VII)

wherein the substituents $R^1$-$R^6$ and $X^1$—$X^4$ are defined herein and $P^1$ and $P^2$ are, independently, a suitable oxygen protecting group. See Peter G. M Wuts and Theodora W. Greene, Greene's Protective Groups in Organic Synthesis (4$^{th}$ ed. 2007) for other commonly-used protecting groups for hydroxyl groups. It should be understood that the compound of formula (VI) can be modified to access compounds where $X^2$ is other than O by using, for example, a compound where the $OP^2$ group is replaced by a $NR^6P^3$ group, wherein $P^3$ is a suitable amine protecting group.

In some examples, the compounds of the formula (VI) and (VII) can be synthesized from a compound of the formula (VIII) and (IX), respectively:

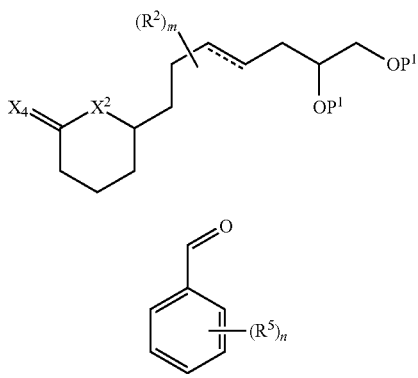

(VIII)

(IX)

wherein the substituents $R^1$-$R^6$ and $X^1$—$X^4$ are defined herein and $P^1$ and $P^4$ are, independently, a suitable oxygen protecting group. See Peter G. M Wuts and Theodora W. Greene, Greene's Protective Groups in Organic Synthesis (4$^{th}$ ed. 2007) for other commonly-used protecting groups for hydroxyl groups. It should be understood that the compound of formula (VIII) can be modified to access compounds where $X^3$ is other than O by using, for example, a compound where the $OP^4$ group is replaced by a $NR^6P^5$ group, wherein $P^5$ is a suitable amine protecting group. In addition, it should be understood that one or more groups $R^2$ can also be on the ring comprising $X^2$.

Some examples include methods of making a compound of the formula (III) with a the compound of the formula (X):

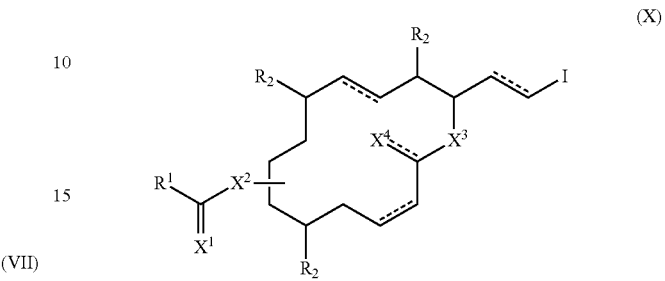

(X)

such that the compound of the formula (III) is a compound of the formula:

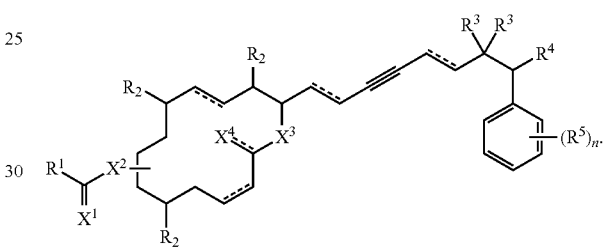

Other examples include methods of making a compound of the formula (III) with a the compound of the formula (XI):

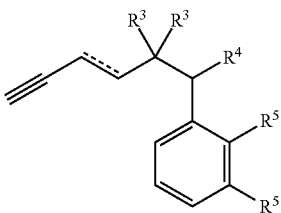

(XI)

such that the compound of the formula (III) is a compound of the formula:

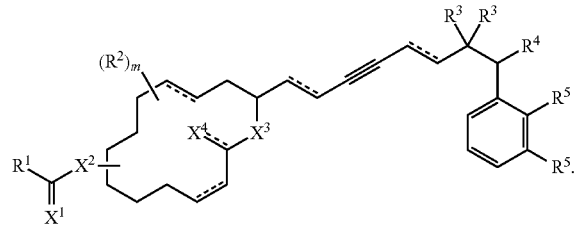

Still other examples include methods of making a compound of the formula (III) with the compound of the formula (X) and a compound of the formula (XI) to give a compound of the formula:

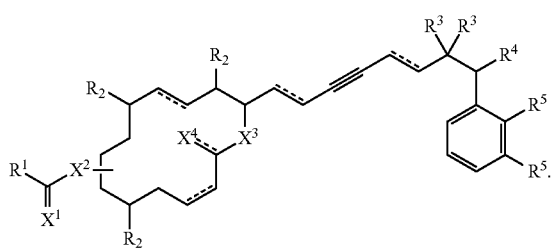

Those of ordinary skill in the art will recognize that compounds described herein can contain chiral centers. All diastereomers of the compounds described herein are contemplated herein, as well as racemates.

Various examples of the present invention also contemplate pharmaceutical compositions comprising one or more compounds of the various examples of the present invention (e.g., compounds of the formula (I)-(III)) and one or more pharmaceutically acceptable carriers, diluents, excipients or combinations thereof. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one example, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions of the present invention may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions of the present invention may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited examples, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various examples of the present invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds of the present invention or an appropriate pharmaceutical composition thereof are effective, the compounds of the present invention may be administered in an effective amount. The dosages as suitable for this invention may be a composition, a pharmaceutical composition or any other compositions described herein.

For each of the recited examples, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one example, the dosage may be administered daily for up to and including 30 days, preferably between 7-10 days. In another example, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred mutes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

In some examples, the various examples of the present invention contemplate compositions comprising a therapeutically effective amount of one or more compounds of the various examples of the present invention. In some aspects, the various examples of the present invention contemplate a compound of the formulae (I)-(III) for use as a medicament for treating a patient in need of relief from a disease or a condition, such as cancer.

The term "therapeutically effective amount" as used herein, refers to that amount of one or more compounds of the various examples of the present invention that elicits a biological or medicinal response in a tissue system, animal or human, that is being sought by a researcher, veterinarian, medical doctor or other clinician, which includes alleviation of the symptoms of the disease or disorder being treated. In some examples, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

In some examples, the compounds of the various examples of the present invention have a half maximal inhibitory concentration ($IC_{50}$) of from about 5 nM to about 500 nM (e.g., about 50 nM to about 100 nM, about 10 nM to about 75 nM, about 10 nM to about 60 nM, about 100 nM to about 500 nM, about 50 µM to about 250 nM, about 100 nM to about 300 nM or about 10 nM to about 30 nM).

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substituted" as used herein refers to a group (e.g., alkyl, aryl, and heteroaryl) or molecule in which one or more hydrogen atoms contained thereon are replaced by one or more substituents. The term "substituent" as used herein refers to a group that can be or is substituted onto a molecule or onto a group. Examples of substituents include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be, for example, hydrogen, alkyl, acyl, cycloalkyl, aryl, aralkyl, heterocyclyl, heteroaryl, or heteroarylalkyl.

The term "alkyl" as used herein refers to substituted or unsubstituted straight chain and branched alkyl groups and cycloalkyl groups having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$), or, in some examples, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed herein, for example, amino, hydroxy, cyano, carboxy, nitro, thio, alkoxy, and halogen groups.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some examples, the cycloalkyl group can have 3 to about 8-12 ring members, whereas in other examples the number of ring carbon atoms range from 3 to 4, 5, 6, or 7. In some examples, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some examples, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups.

The term "heterocyclyl" as used herein refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. In some examples, heterocyclyl groups include 3 to about 20 ring members, whereas other such groups have 3 to about 15 ring members. In some examples, heterocyclyl groups include heterocyclyl groups that include 3 to 8 carbon atoms ($C_3$-$C_8$), 3 to 6 carbon atoms ($C_3$-$C_6$), 3 to 5 carbon atoms ($C_3$-$C_5$), 3 to 4 carbon atoms ($C_3$-$C_4$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocydyl ring can also include one or more double bonds. A heteroaryl ring is an example of a heterocydyl group. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazyolyl, tetrazolyl, benzoxazolinyl, and benzimidazolinyl groups.

The term "alkoxy" as used herein refers to an oxygen atom connected to an alkyl group, including a cycloakyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cydohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to alkylamines, arylamines, arylalkylamines; dialkylamines, diarylamines, diaralkylamines, heterocyclylamines and the like; and ammonium ions.

The terms "halo," "halogen," or "halide" group, as used herein, by themselves or as part of another substituent, mean, unless otherwise stated, a fluorine, chlorine, bromine, or iodine atom.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

EXAMPLES

The present invention can be better understood by reference to the following examples which are offered by way of illustration. The present invention is not limited to the examples given herein.

Synthetic Overview
The retrosynthesis of callyspongiolide is outlined in Scheme 1.
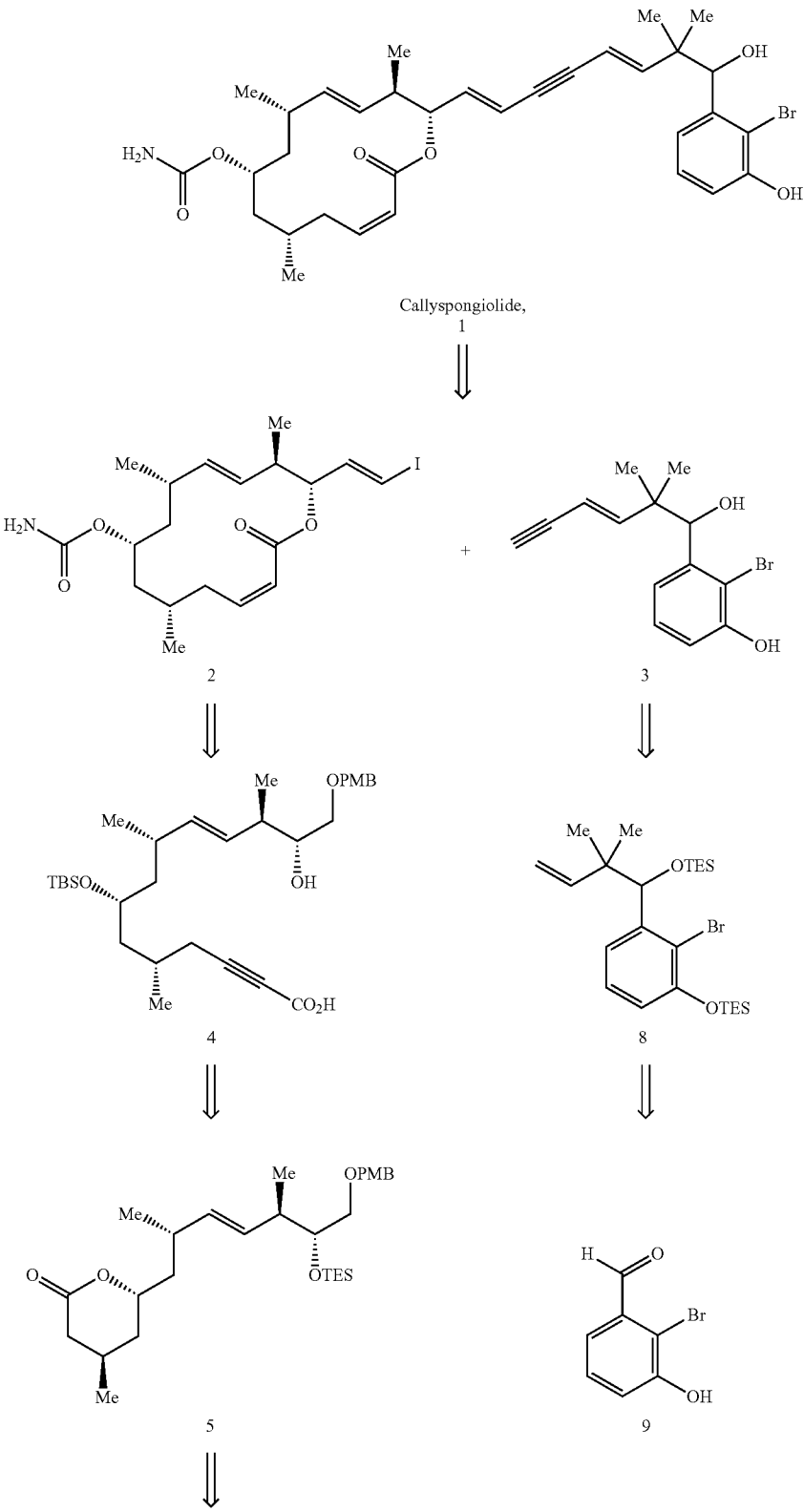

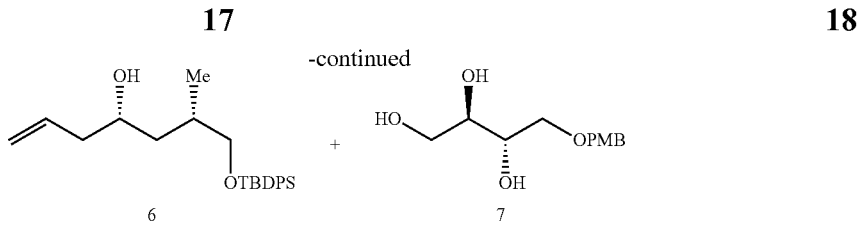

A late-stage Sonogashira coupling of vinyl iodide 2 with either enantiomer of enyne 3 would allow access to both antipodes of the proposed molecule. The macrolactone is constructed by macrolactonization of seco acid 4, which is accessible via ring-opening of lactone 5. The "congested" olefin of 5 would be formed through a modified Julia olefination using a sulfone derived from known diol 7 and an aldehyde obtained from known allyl alcohol 6. Wittig olefination with the aldehyde derived from olefin 8 gives enyne 3. Stereoselective Corey-Bakshi-Shibata (CBS) reduction of a hindered ketone derived from commercially available aldehyde 9 would provide access to both isomers.

The synthesis of callyspongiolide begins from known chiral alcohol 6 as shown in Scheme 2, which is prepared in four steps from commercially available (S)-(+)-3-bromo-2-methyl-1-propanol. Treatment of allyl alcohol 6 with acryloyl chloride and triethylamine gave diene 11, which was then subjected to ring closing metathesis using Grubbs II catalyst to give α,β-unsaturated lactone 12. 1,4-addition using Me₂CuLi₂I delivered the methyl substituent stereoselectively to the bottom face of the molecule, providing the corresponding 4,6-anti-substituted lactone 13 in 95% yield as a single diastereomer (determined by ¹H NMR). Treatment of the tert-butyl diphenylsilyl (TBDPS) ether with tetrabutyl ammonium fluoride (TBAF) smoothly afforded the corresponding alcohol, which upon oxidation using Dess-Martin periodinane DMP in the presence of NaHCO₃ furnished aldehyde 14 in 90% yield.

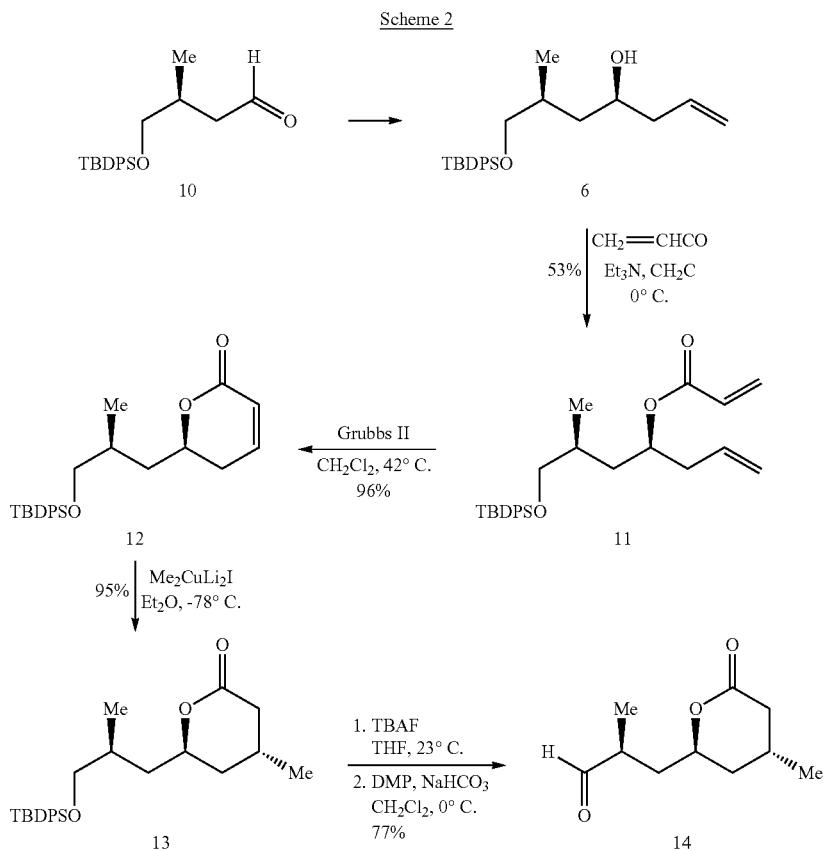

Scheme 2

Known diol 7 is readily prepared in four steps from commercially available 2-butyne-1,4-diol as described by Crimmins et al. Selective Mitsunobu displacement with 1-phenyl-1H-tetrazole-5-thiol (PTSH, 16) followed by protection of the latent secondary alcohol provided sulfide 17. See Scheme 3. Oxidation using m-chrloroperbenzoic acid (m-CPBA) afforded sulfone 18, which was now set for the modified Julia olefination reaction. Metallation using lithium hexamethyldisilazide (LHMDS) in dimethyl formamide (DMF) at −60° C. followed by addition of aldehyde 14 gave the desired trans-disubstituted olefin 5 in 74% yield with a trans/cis ratio of 34:1 as determined by ¹H NMR.

Scheme 3

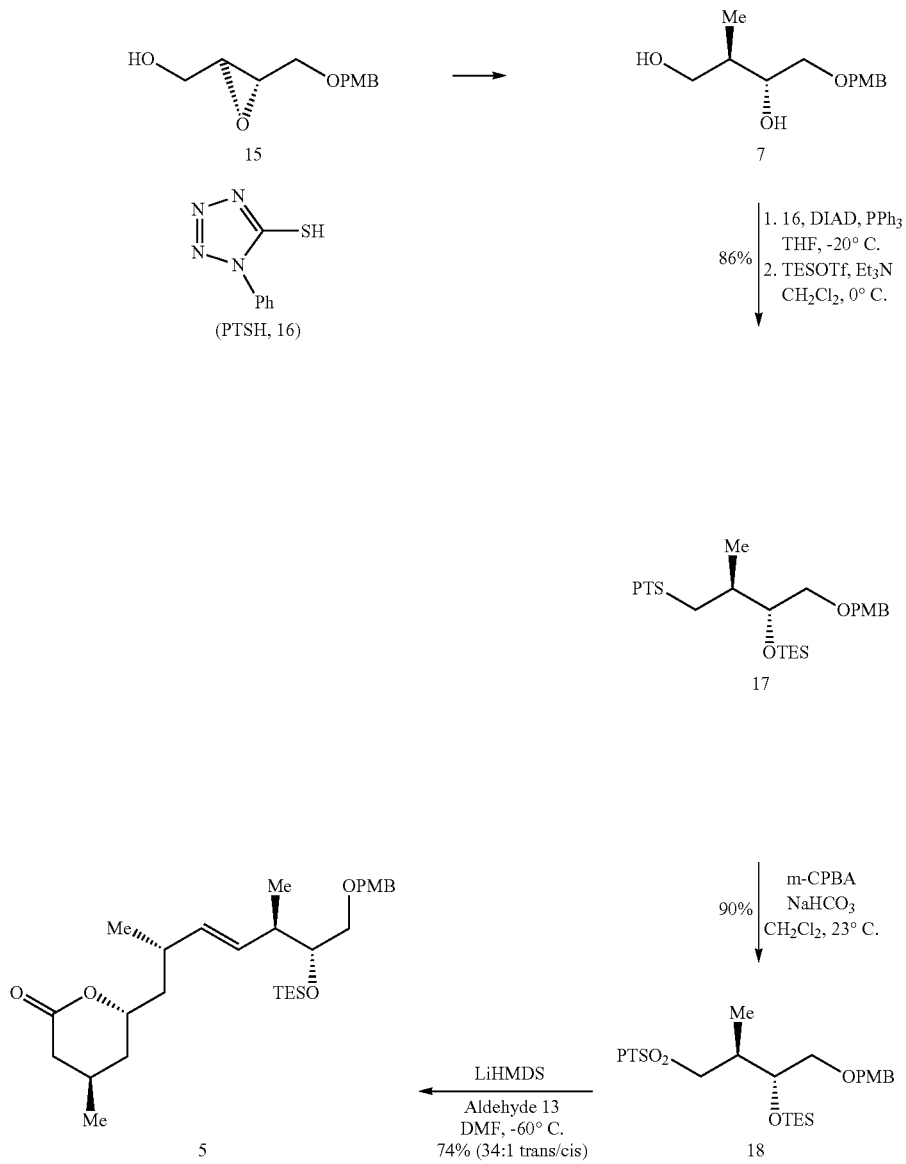

The lactone 5 was opened using N,O-dimethylhydroxylamine hydrochloride and $^i$PrMgCl in tetrahydrofuran (THF) at −20° C. to provide the corresponding Weinreb amide (Scheme 4). The secondary alcohol was protected as the tert-butyl dimethyl silyl (TBS) ether with TBSCl and trimethylamine in either DMF or dichloromethane (DCM) to obtain TBS ether 19 in 85% yield over two steps. Reduction using diisobutyl aluminum hydride (DIBAL-H) followed by treatment with the Ohira-Bestmann reagent and K$_2$CO$_3$ in MeOH gave the homologated alkyne 20. The terminal acetylene moiety was alkylated by metallation with n-BuLi in THF at −78° C. followed by treatment with ethyl chloroformate to give alkynyl ester 21. Selective removal of the triethyl silyl (TES) ether using pyridinium p-toluenesulfonate (PPTS) in methanol at 0° C. followed by LiOH-mediated ester hydrolysis provided the corresponding seco acid. Yonemitsu's variation for macrolactonization proved highly effective, whereby the mixed anhydride is not preformed but rather the seco acid is directly added to 2,4,6-trichlorobenzoyl chloride, 4-dimethylaminopyridine (DMAP), and amine base from the beginning to furnish alkynyl lactone 22 in 67% yield over 3 steps. Reduction of the alkynyl moiety was accomplished by using Lindlar catalyst poisoned with quinoline under a hydrogen balloon. Removal of the TBS ether was ineffective using tetra-n-butylammonium fluoride (TBAF), even at elevated temperatures. Alternatively, use of HF.pyridine was highly efficient and gave the corresponding alcohol. Chlorosulfonyl isocyanate was used to install the carbamate moiety in 80% yield over both steps. Removal of the para-methoxybenzyl (PMB) protecting group was accomplished using 2,3-dichloro-5,6-dicyanobenzoquinone (DDQ) to provide the corresponding alcohol, which was oxidized using DMP and then subjected to Takai olefination to furnish vinyl iodide 2 in 42% yield over three steps.

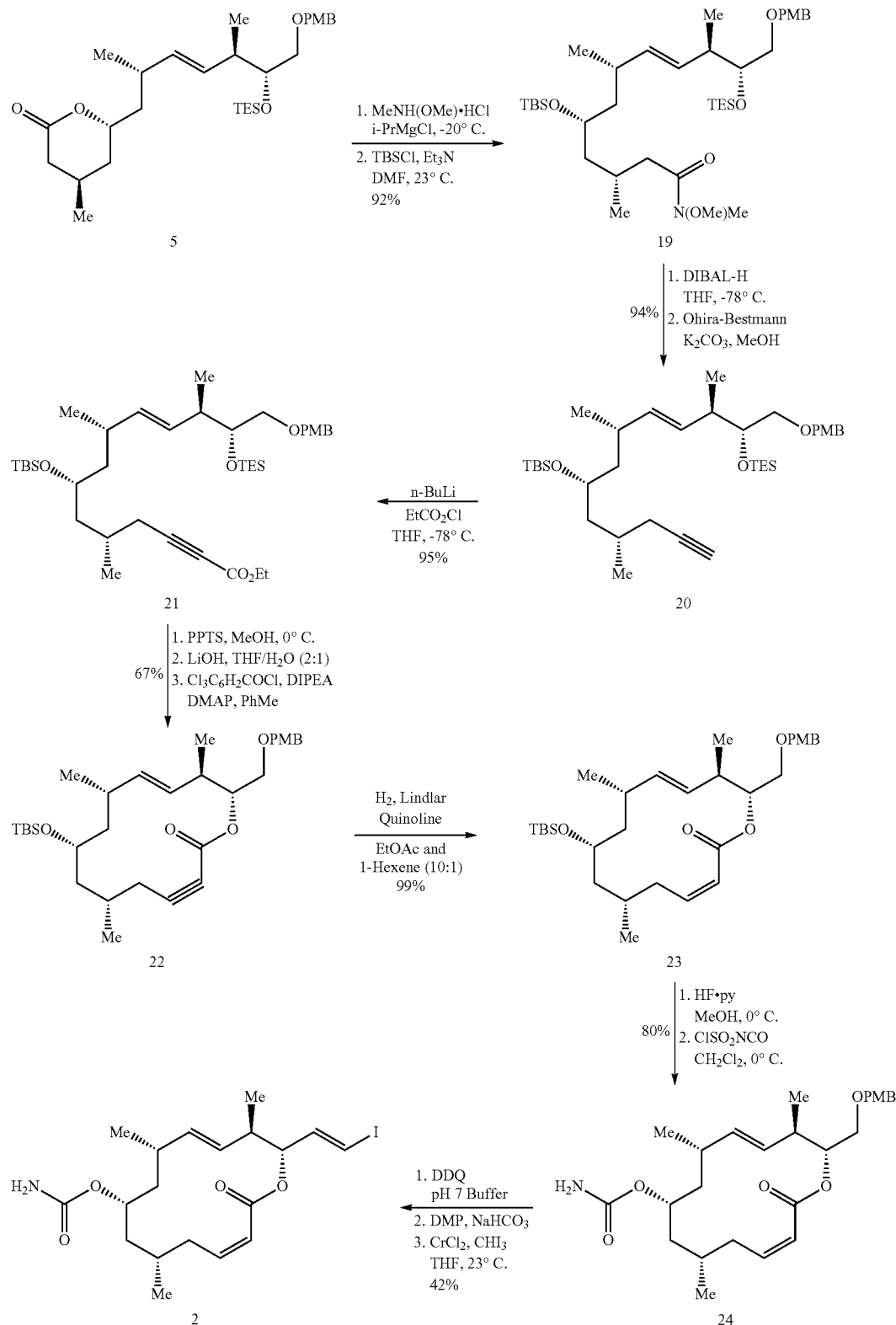
Scheme 4
Commercially available 2-bromo-3-hydroxybenzaldehyde (9) was protected as the TBS phenol (Scheme 5) followed by reverse prenylation using 3-methyl-2-butenylmagnesium chloride to give alcohol 8 in 98% yield over 2 steps. The racemic alcohol was oxidized using pyridinium chlorochromate (PCC)/SiO$_2$ in DCM to give the corresponding ketone, which was subjected to chiral reduction using Corey's (S)-Me-CBS catalyst to furnish alcohol (S)-8 in 57% yield and 95% ee (determined by chiral HPLC). Synthesis and X-ray crystallography of the 4-nitrobenzoate derivative confirmed the stereochemical outcome. Triethylsilyl triflate (TESOTf) protected the hindered alcohol. Ozonolysis of the terminal olefin gave a mixture of products, including silyl deprotection. Nicolau's conditions for oxidative cleavage of olefins provided the corresponding aldehyde, which was then subjected to Wittig olefination with commercially available phosphonium bromide 26 to give the corresponding TMS-protected enyne in a trans/cis ratio of 7:1. Global deprotection of all silyl protecting groups was achieved using TBAF to afford enyne (S)-3 in 53% yield over 3 steps. In the same manner, (R)-3 was prepared using the same chemistry while employing (R)-Me-CBS during the chiral reduction.

Scheme 5

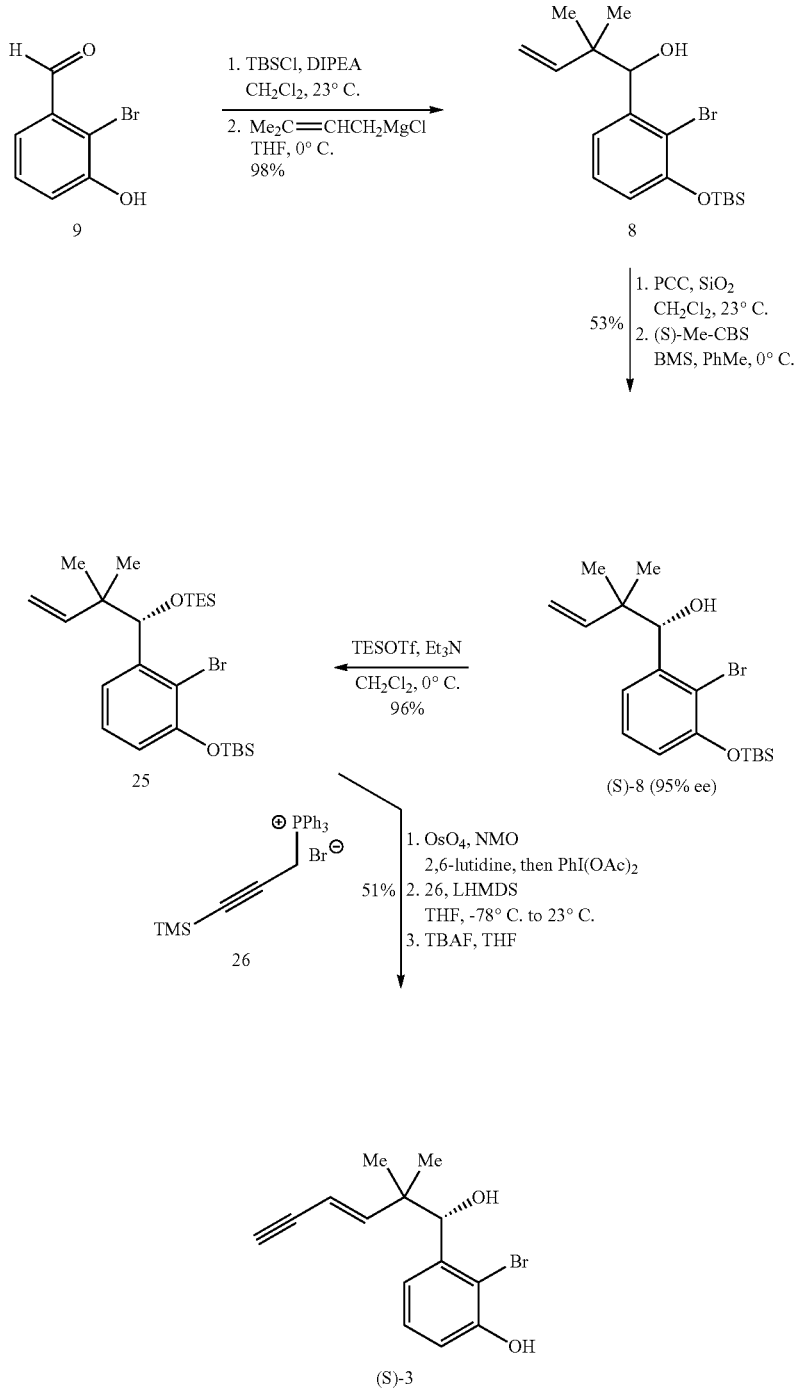

Sonogashira coupling of vinyl iodide 2 with (S)-3 gave the desired dienyne (S)-1 in 42% yield over 3 steps (Scheme 6). Similarly, coupling with the (R)-enantiomer furnished dienyne (R)-1 in 39% yield over 3 steps.
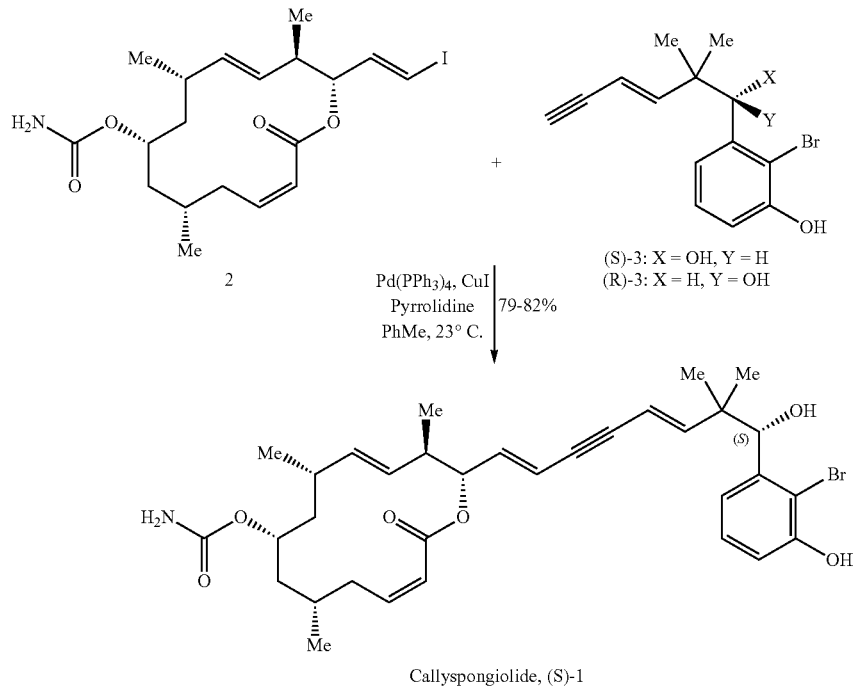
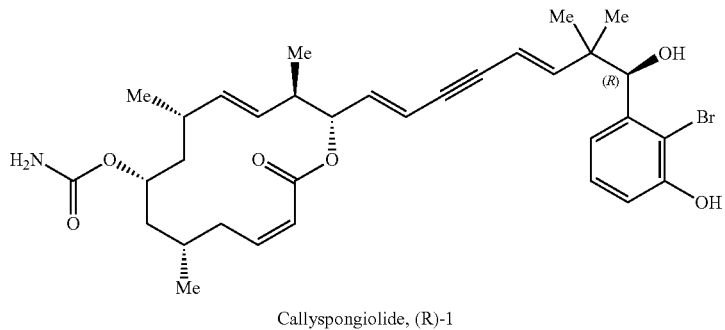
This synthetic methods presented herein provide access to analogs of the compound of formula (I) and/or (II), such as compounds 28-39:
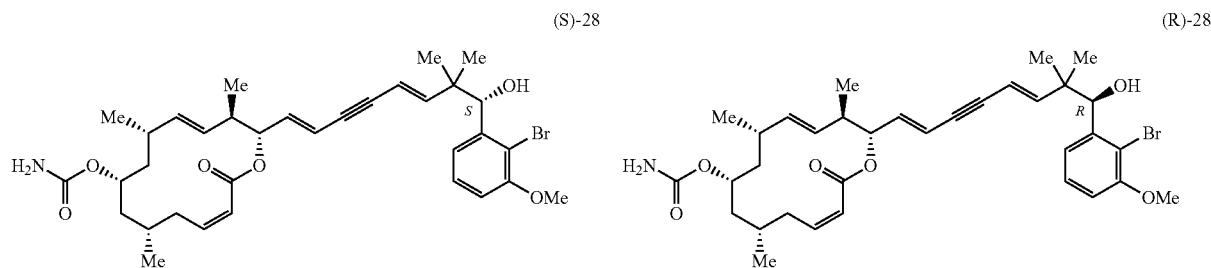

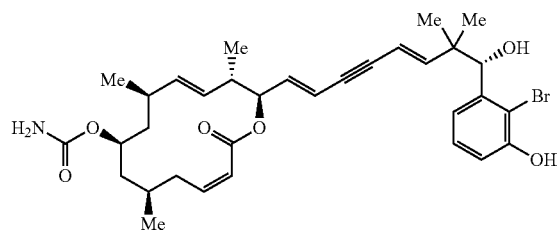
29
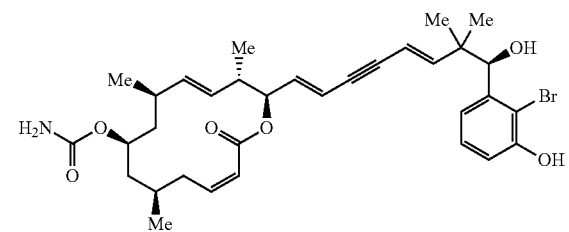
30
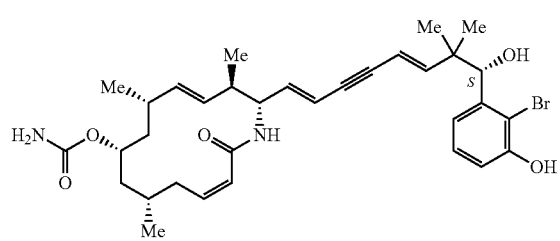
31
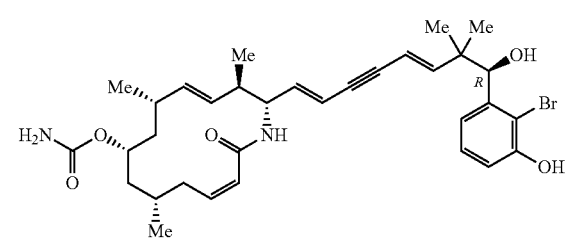
32
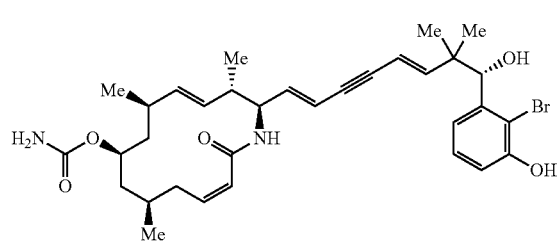
33
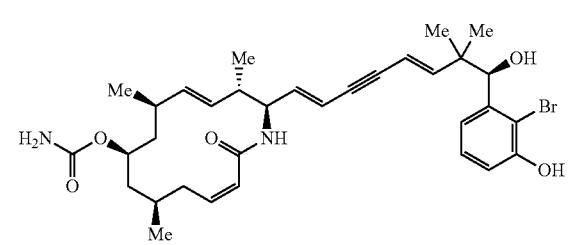
34
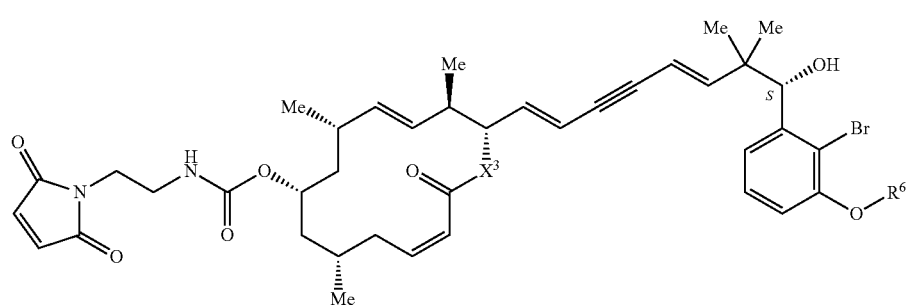
(S)-35
X = O, NR$^6$
(R$^6$ = H, alkyl)
(R$^6$ = H, alkyl)
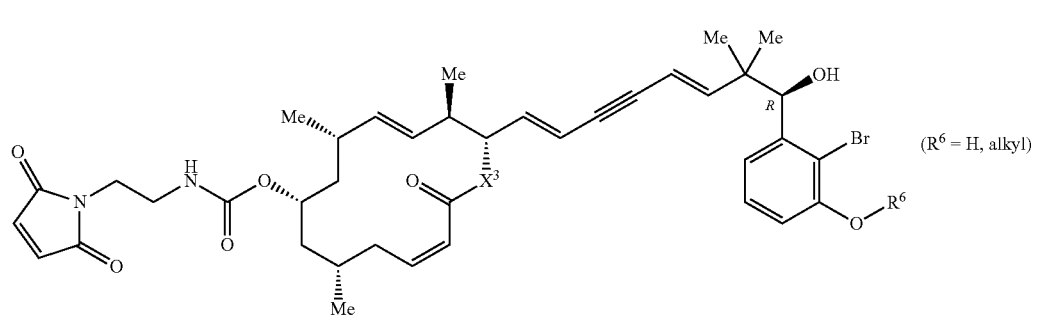
(R)-35
(R$^6$ = H, alkyl)
X = O, NR$^6$
(R$^6$ = H, alkyl)

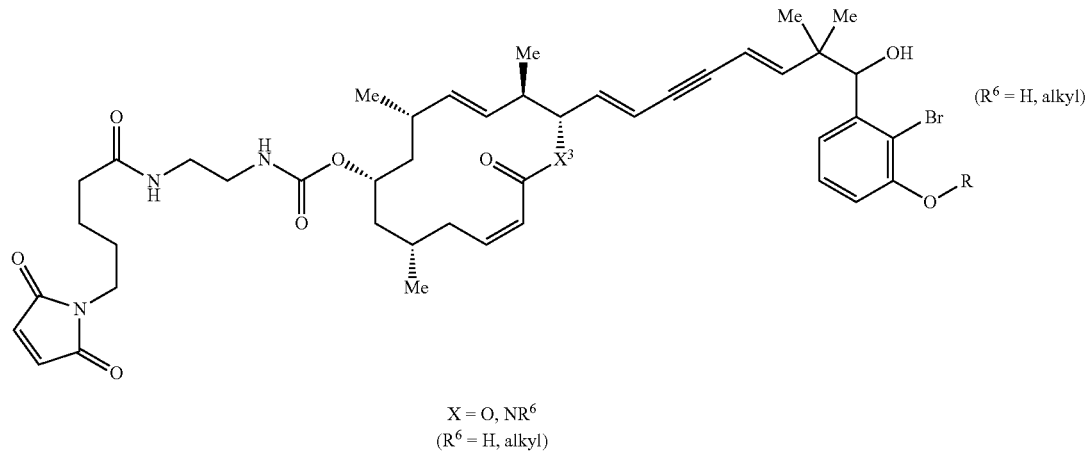
36
$X = O, NR^6$
($R^6$ = H, alkyl)
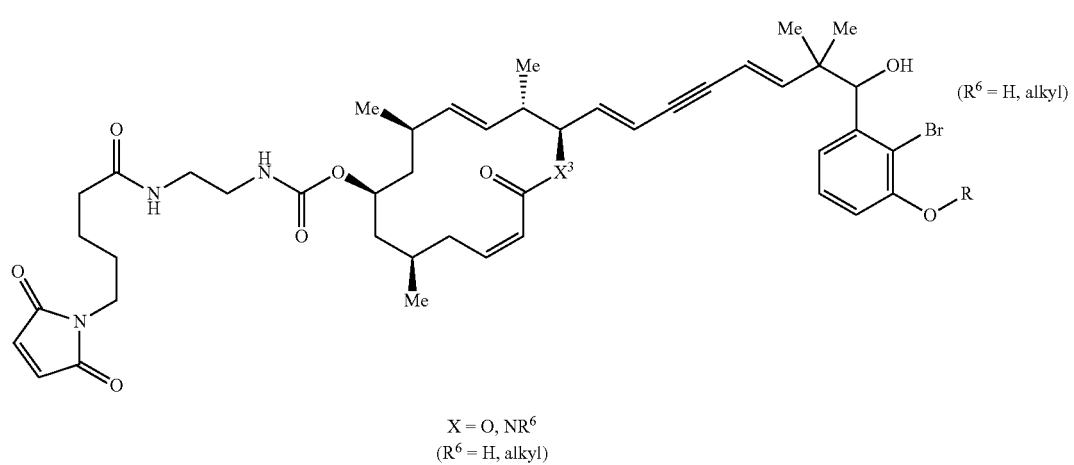
37
$X = O, NR^6$
($R^6$ = H, alkyl)
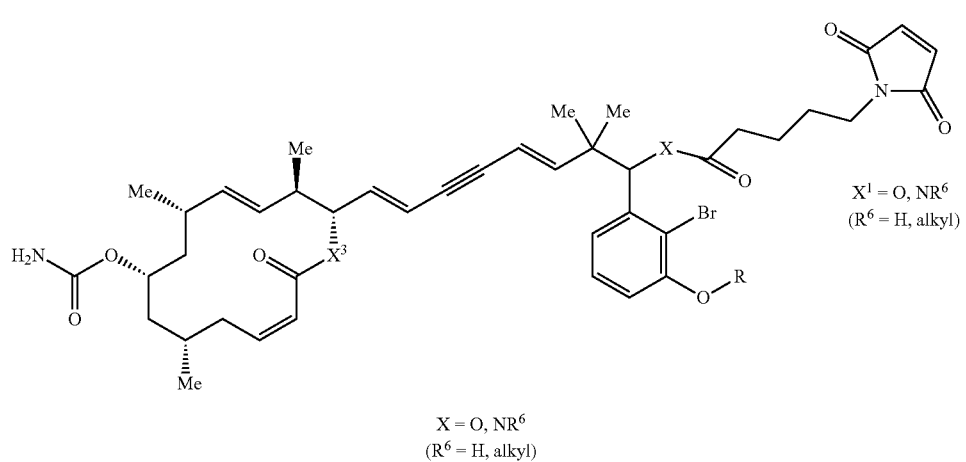
38
$X^1 = O, NR^6$
($R^6$ = H, alkyl)
$X = O, NR^6$
($R^6$ = H, alkyl)

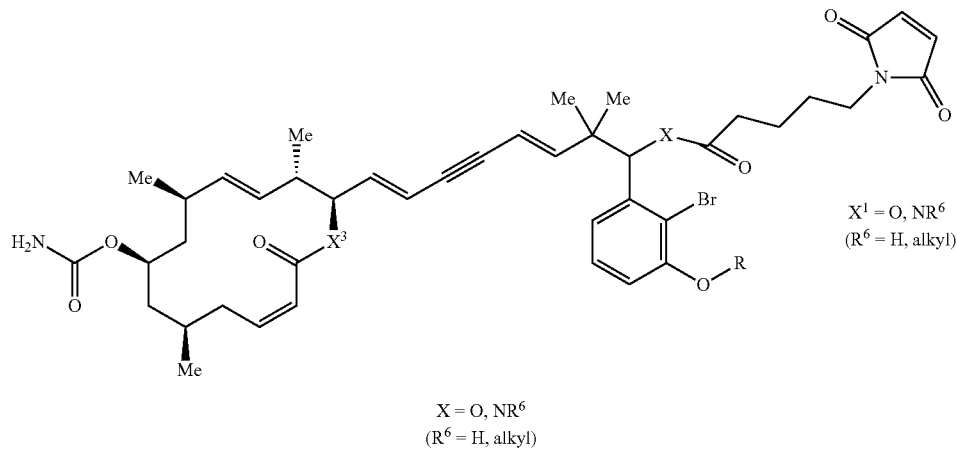

X = O, NR⁶
(R⁶ = H, alkyl)

X¹ = O, NR⁶
(R⁶ = H, alkyl)

Synthesis of Diene 11:

To a clear solution of alcohol (5.3783 g, 14.1 mmol) in DCM (100 mL) at 0° C. was added Et₃N (9.8 mL, 70.3 mmol, 5 equiv.) and acryloyl chloride (2.3 mL, 28.3 mmol, 2 equiv.) sequentially. After 30 minutes, silica gel was added and the mixture was concentrated via rotary evaporation. The crude product was purified by column chromatography (3% EA/HX) to give 32532 g (53% yield) of diene as a clear oil.

$R_f$=0.4 (5% EA/HX); ¹H NMR (500 MHz, CDCl₃) d (ppm): 7.67-7.71 (m, 4H), 7.38-7.47 (m, 6H), 6.38 (dd, J=17.3, 1.5 Hz, 1H), 6.10 (dd, J=17.3, 10.4 Hz, 1H), 5.74-5.83 (m, 2H), 5.07-5.13 (m, 3H), 3.50-3.57 (m, 2H), 2.30-2.42 (m, 2H), 1.81-1.88 (m, 1H), 1.74-1.80 (m, 1H), 1.46 (ddd, J=14.0, 8.1, 6.8 Hz, 1H), 1.09 (s, 9H), 1.00 (d, J=6.8 Hz, 3H); ¹³C NMR (125 MHz, CDCl₃) d (ppm): 17.6, 19.5, 27.0, 32.8, 37.0, 39.0, 68.2, 72.4, 117.9, 127.7, 129.0, 129.7, 130.4, 133.7, 134.0, 135.7, 165.9; $[\alpha]_D^{20}$ 8.88 (c 2.97, chloroform).

Synthesis of a,b-Unsaturated Lactone 12:

A deep violet solution of diene (5.7564 g, 13.2 mmol) and Grubbs II catalyst (586.2 mg, 0.690 mmol, 5.2 mol %) in DCM (750 mL) was heated to reflux while covered in aluminum foil. The reaction was quenched with ethyl vinyl ether (0.66 mL, 6.89 mmol, 0.5 equiv) after 14 hrs. and left stirring 1 hr. Concentration via rotary evaporation followed by column chromatography purification (10% EA/HX) gave 5.5139 g (96% yield) of α,β-unsaturated lactone as a clear oil.

$R_f$=0.2 (10% EA/HX); ¹H NMR (500 MHz, CDCl₃) d (ppm): 7.64-7.68 (m, 4H), 7.36-7.45 (m, 6H), 6.83 (ddd, J=9.7, 5.4, 3.2 Hz, 1H), 6.00 (ddd, J=9.8, 2.4, 1.2 Hz, 1H), 4.43 (m, 1H), 3.59 (dd, J=10.1, 5.2 Hz, 1H), 3.54 (dd, J=10.1, 5.6 Hz, 1H), 2.18-2.31 (m, 2H), 1.91-2.00 (m, 1H), 1.80 (ddd, J=14.1, 72, 5.3 Hz, 1H), 1.67 (ddd, J=14.5, 8.1, 6.7 Hz, 1H), 1.07 (s, 9H), 0.99 (d, J=6.9 Hz, 3H); ¹³C NMR (125 MHz, CDCl₃) d (ppm): 164.6, 145.0, 135.7, 133.8, 129.8, 127.8, 121.5, 76.7, 68.1, 38.7, 31.8, 29.8, 27.0, 19.4, 17.6; $[\alpha]_D^{20}$, -49.79 (c 2.36, chloroform).

Synthesis of Lactone 13:

To a tan suspension of CuI (3.1795 g, 16.7 mmol, 2.0 equiv.) in Et₂O (60 mL) at 0° C. was added MeLi (3.1 M DEM, 10.8 mL, 33.5 mmol, 4.0 equiv.) slowly. After stirring 30 minutes, the clear solution was cooled to −78° C. and a clear solution of lactone (3.4087 g, 8.34 mmol) in Et₂O (20 mL) was added slowly via cannula. The flask was allowed to warm to −10° C. over the course of 3 hrs. and then quenched with sat. NH₄Cl. The crude product was extracted with EA (×3), washed in brine and dried over Na₂SO₄. Purification by flash chromatography (10% EA/HX) gave 3.3657 g (95% yield) of lactone as a clear oil.

$R_f$=0.3 (15% EA/HX); ¹H NMR (400 MHz, CDCl₃) d (ppm): 7.64 (d, J=7.1 Hz, 4H), 7.35-7.46 (m, 6H), 4.42 (sep, J=4.3 Hz, 1H), 3.46-3.60 (m, 2H), 2.53 (dd, J=15.9, 5.2 Hz, 1H), 2.05-2.18 (m, 2H), 1.85-1.96 (m, 1H), 1.65-1.75 (m, 2H), 1.46-1.75 (m, 2H), 1.46-1.60 (m, 3H), 1.03-1.07 (m, 12H), 0.96 (d, J=6.7 Hz, 3H).

Synthesis of Aldehyde 14:

To a clear solution of TBDPS ether (3.3779 g, 7.95 mmol) in THF (40 mL) was added TBAF (1 M THF, 16.7 mL, 16.7 mmol, 2 equiv.) slowly. After 45 minutes, the reaction was quenched with sat. NH₄Cl. The crude product was extracted with EA (×3), washed in brine, and dried over Na₂SO₄. Purification by flash chromatography (50% EA/HX) gave 1.2741 g of alcohol as a clear oil.

To a clear solution of alcohol (1.2741 g, 6.84 mmol) in DCM (40 mL) at 0° C. was added portionwise NaHCO₃ (2.8733 g, 34.2 mmol, 5.0 equiv.) and DMP (5.8023 g, 13.7 mmol, 2.0 equiv.) sequentially. After 10 minutes, the ice bath was removed and the reaction stirred for a further 1.5 hrs. at room temperature. The reaction was quenched with a 1:1 solution of sat. NaHCO₃/Na₂S₂O₃ solution and left stirring vigorously 10 minutes. The crude product was then extracted with DCM (×3), washed in brine, and dried over MgSO₄. Purification through a short silica plug (40% EA/HX) gave 1.1286 mg (77% yield over 2-steps) of aldehyde as a clear oil.

$R_f$=0.4 (50% EA/HX); ¹H NMR (500 MHz, CDCl₃) d (ppm): 9.66 (s, 1H), 4.43-4.50 (m, 1H), 2.73-2.81 (m, 1H), 2.51-2.57 (m, 1H), 2.10-2.22 (m, 2H), 1.92-2.00 (m, 1H), 1.72-1.79 (m, 1H), 1.57-1.67 (m, 1H), 1.17 (d, J=7.5 Hz, 3H), 1.08 (d, J=6.7 Hz, 3H); ¹³C NMR (125 MHz, CDCl₃) d (ppm): 204.0, 172.3, 75.2, 42.5, 37.5, 36.5, 35.6, 24.0, 21.4, 14.6.

Synthesis of Sulfide 17:

To a clear solution of diol (3.3165 g, 13.8 mmol), PPh₃ (5.0855 g, 19.4 mmol, 1.4 equiv.), and PTSH (3.4498 g, 19.4 mmol, 1.4 equiv.) in THF (140 mL) at −20° C. was DIAD (3.8 mL, 19.3 mmol, 1.4 equiv.) slowly. After 1 hr, silica gel was added and the mixture concentrated via rotary evaporation. Purification by flash chromatography (30% EA/HX) gave 4.9748 g of sulfide as a clear oil.

To a clear solution of alcohol (4.9748 g, 12.4 mmol) in DCM (100 mL) at 0° C. was added Et$_3$N (9.0 mL, 64.6 mmol, 5.2 equiv.) and TESOTf (5.6 mL, 24.8 mmol, 2.0 equiv.) sequentially. After 45 minutes the reaction was quenched with sat. NaHCO$_3$ and the flask warmed to room temperature. The crude product was extracted with DCM (×3), washed in brine, and dried over MgSO$_4$. Purification by flash chromatography (5% EA/HX) gave 5.6118 g (88% yield over 2-steps) of sulfide as a clear oil.

R$_f$=0.6 (25% EA/HX); $^1$H NMR (500 MHz, CDCl$_3$) d (ppm): 7.50-7.59 (m, 5H), 7.24 (d, J=8.6 Hz, 2H), 6.86 (d, J=8.7 Hz, 2H), 4.44 (s, 2H), 3.83 (m, 1H), 3.79 (s, 3H), 3.64 (dd, J=12.9, 4.8 Hz, 1H), 3.51 (dd, J=9.7, 6.1 Hz, 1H), 3.43 (dd, J=9.7, 5.4 Hz, 1H), 3.29 (dd, J=12.8, 7.1 Hz, 1H), 2.20-2.28 (m, 1H), 1.06 (d, J=7.0 Hz, 3H), 0.92 (t, J=8.1 Hz, 9H), 0.53-0.61 (m, 6H); $^{13}$C NMR (125 MHz, CDCl$_3$) d (ppm): 159.3, 155.1, 133.9, 1302, 130.1, 129.8, 129.5, 123.9, 113.8, 74.4, 73.1, 72.3, 55.4, 36.4, 35.9, 16.3, 7.0, 5.1; [α]$_D^{20}$ 14.99 (c 2.45, chloroform).

Synthesis of Sulfone 18:

To a clear solution of sulfide (7.1321 g, 13.9 mmol) in DCM (70 mL) was added portionwise NaHCO$_3$ (11.6666 g, 139 mmol, 10 equiv.) and m-CPBA (70 wt %, 17.1966 g, 69.8 mmol) sequentially. After 13 hrs, the flask was cooled to 0° C. and carefully quenched with sat. NaHSO$_3$. The crude product was extracted with DCM (×3), washed in sat. NaHCO$_3$, brine, and dried over MgSO$_4$. Purification by flash chromatography (5% EA/HX) gave 7.5755 g (90% yield) of sulfone as a clear oil.

R$_f$=0.3 (10% EA/HX); $^1$H NMR (500 MHz, CDCl$_3$) d (ppm): 7.64-7.68 (m, 2H), 7.56-7.64 (m, 3H), 7.24 (d, J=8.7 Hz, 2H), 6.87 (d, J=8.7 Hz, 2H), 4.43 (s, 2H), 4.11 (dd, J=15.0, 2.8 Hz, 1H), 3.83 (ddd, J=6.5, 5.7, 2.9 Hz, 1H), 3.80 (s, 3H), 3.48 (dd, J=14.9, 9.4 Hz, 1H), 3.38-3.44 (m, 2H), 2.53-2.61 (m, 1H), 1.20 (d, J=7.0 Hz, 3H), 0.93 (t, J=8.2 Hz, 9H), 0.55-0.62 (m, 6H); $^{13}$C NMR (125 MHz, CDCl$_3$) d (ppm): 159.3, 154.1, 133.2, 131.5, 130.0, 129.7, 129.5, 125.3, 113.9, 74.2, 73.1, 71.5, 57.9, 55.3, 31.6, 17.3, 6.9, 5; [α]$_D^{20}$ 7.20 (c 3.10, chloroform).

Synthesis of Lactone 5:

To a clear solution of sulfone (2.3409 g, 4.28 mmol, 1.6 equiv.) in DMF (20 mL) at −60° C. was added LHMDS (1 M THF, 4.7 mL, 4.7 mmol, 1.8 equiv.) slowly over 5 minutes. After stirring 45 minutes, a clear solution of aldehyde (481.7 mg, 2.62 mmol) in DMF (7 mL) was added slowly via cannula. After 1.5 hrs, the reaction was quenched with sat. NH$_4$Cl and flask warmed to room temperature. The crude product was diluted with H$_2$O and extracted with EA (×3), washed in brine, and dried over Na$_2$SO$_4$. Purification by flash chromatography (10% EA/HX) gave 976.6 mg (74% yield, 34:1 trans/cis) of lactone as a clear oil.

R$_f$=0.5 (25% EA/HX); $^1$H NMR (500 MHz, CDCl$_3$) d (ppm): 723 (d, J=8.7 Hz, 2H), 6.87 (d, J=8.8 Hz, 2H), 5.42 (dd, J=15.6, 8.2 Hz, 1H), 5.15 (dd, J=15.6, 8.4 Hz, 1H), 4.44 (d, J=11.6 Hz, 2H), 4.33-4.41 (m, 2H), 3.80 (s, 3H), 3.71 (td, J=5.8, 3.3 Hz, 1H), 3.32 (dd, J=9.3, 5.8 Hz, 1H), 3.27 (dd, J=9.3, 5.8 Hz, 1H), 2.50-2.57 (m, 1H), 2.38-2.46 (m, 1H), 2.34 (td, J=7.2, 3.3 Hz, 1H), 2.07-2.18 (m, 2H), 1.63-1.76 (m, 2H), 1.46 (ddd, J=14.1, 5.8, 4.1 Hz, 1H), 1.29 (ddd, J=13.9, 10.0, 3.5 Hz, 1H), 1.04 (d, J=6.6 Hz, 3H), 0.99 (d, J=7.0 Hz, 3H), 0.96 (d, J=6.9 Hz, 3H), 0.93 (t, J=8.0 Hz, 9H), 0.54-0.62 (m, 6H); $^{13}$C NMR (125 MHz, CDCl$_3$) d (ppm): 172.7, 159.2, 135.2, 131.7, 130.7, 129.3, 113.8, 75.5, 75.1, 73.0, 72.9, 55.4, 43.0, 40.4, 37.6, 35.7, 33.8, 33.3, 24.0, 21.7, 17.3, 7.1, 5.2; [α]$_D^{20}$ 71.2 (c 1.39, chloroform).

Synthesis of Weinreb Amide 19:

To a cloudy mixture of lactone (939.0 mg, 1.86 mmol) and amine salt (371.5 mg, 3.81 mmol, 2.0 equiv.) in THF (19 mL) at −20° C. was added $^i$PrMgCl (2 M THF, 4.6 mL, 9.20 mmol, 5.0 equiv.) slowly. After 45 minutes, the reaction was quenched with sat. NH$_4$Cl and flask warmed to room temperature. The crude product was extracted with EA (×3), washed in brine, and dried over Na$_2$SO$_4$. Purification by flash chromatography (30% EA/HX) gave 968.4 mg of Weinreb amide as a clear oil.

To a clear solution of alcohol (968.4 mg, 1.71 mmol) in DMF (17 mL) at 0° C. was added Et$_3$N (950 mL, 6.82 mmol, 4.0 equiv.) and TBSCl (386.7 mg, 2.57 mmol, 1.5 equiv.) sequentially. After 1.5 hours, the reaction was highly diluted with H$_2$O. The crude product was extracted with EA (×3), washed in brine, and dried over Na$_2$SO$_4$. Purification by flash chromatography (10% EA/HX) gave 1.0709 g (92% yield) of TBS ether as a clear oil.

R$_f$=02 (30% EA/HX); $^1$H NMR (500 MHz, CDCl$_3$) d (ppm): 724 (d, J=8.6 Hz, 2H), 6.86 (d, J=8.7 Hz, 2H), 5.41 (dd, J=15.6, 8.1 Hz, 1H), 5.23 (dd, J=15.5, 7.9 Hz, 1H), 4.39 (s, 2H), 3.80 (s, 3H), 3.69-3.76 (m, 2H), 3.66 (s, 3H), 3.37 (dd, J=9.4, 5.1 Hz, 1H), 3.31 (dd, J=9.4, 6.1 Hz, 1H), 3.17 (s, 3H), 2.42 (dd, J=15.1, 5.4 Hz, 1H), 222-2.35 (m, 3H), 2.05-2.14 (m, 1H), 1.42-1.50 (m, 2H), 1.28-1.36 (m, 2H), 0.99 (d, J=7.0 Hz, 3H), 0.91-0.96 (m, 15H), 0.88 (s, 9H), 0.53-0.62 (m, 6H), 0.06 (s, 6H); $^{13}$C NMR (125 MHz, CDCl$_3$) d (ppm): 174.0, 159.2, 136.6, 130.8, 130.2, 129.3, 113.8, 75.3, 73.5, 73.0, 69.1, 61.3, 55.4, 45.6, 44.5, 40.8, 39.7, 33.2, 32.2, 26.8, 26.1, 222, 20.3, 18.2, 17.4, 7.1, 5.2, −3.7, −4.0; [α]$_D^{20}$ 15.7 (c 1.39, chloroform).

Synthesis of Alkyne 20:

To a clear solution of aldehyde (378.6 mg, 0.557 mmol) in THF (5 mL) at −78° C. was added DIBAL-H (1 M HX, 0.85 mL, 0.850 mmol, 1.5 equiv.) slowly. After 30 minutes the reaction was quenched with a few drops of MeOH, diluted with EA, quenched with potassium sodium tartrate and flask warmed to room temperature. After stirring vigorously 1.5 hrs., the crude product was extracted with EA (×3), washed in brine, and dried over Na$_2$SO$_4$. Purification by flash chromatography (5% EA/HX) gave 344.9 mg (quantitative) of aldehyde as a clear oil.

To a white mixture of aldehyde (344.9 mg, 0.555 mmol) and K$_2$CO$_3$ (234.0 mg, 1.69 mmol, 3.0 equiv.) in MeOH (6 mL) was added Ohira-Bestmann reagent (125 mL, 0.833 mmol, 1.5 equiv.) slowly. After 2 hrs., the reaction was quenched with H$_2$O. The crude product was extracted with EA (×3), washed in brine, and dried over Na$_2$SO$_4$. Purification through a short silica plug (40% EA/HX) gave 322.9 mg (94% yield over 2-steps) of aldehyde as a clear oil.

R$_f$=0.5 (5% EA/HX); $^1$H NMR (500 MHz, CDCl$_3$) d (ppm): 7.24 (d, J=8.8 Hz, 2H), 6.87 (d, J=8.8 Hz, 2H), 5.40 (dd, J=15.4, 8.2 Hz, 1H), 5.24 (dd, J=15.6, 7.6 Hz, 1H), 4.37-4.44 (m, 2H), 3.81 (s, 3H), 3.69-3.76 (m, 2H), 3.36 (dd, J=9.4, 5.4 Hz, 1H), 3.31 (dd, J=9.4, 6.0 Hz, 1H), 2.29-2.36 (m, 1H), 2.22-2.29 (m, 1H), 2.20 (ddd, J=16.7, 5.1, 2.6 Hz, 1H), 2.08 (ddd, J=16.6, 7.0, 2.6 Hz, 1H), 1.95 (t, J=2.6 Hz, 1H), 1.74-1.82 (m, 1H), 1.53 (dd, J=13.7, 6.9 Hz, 1H), 1.29-1.43 (m, 3H), 0.97-1.01 (m, 6H), 0.94 (t, J=8.1 Hz, 9H), 0.89 (s, 9H), 0.06 (s, 3H), 0.05 (s, 3H); $^{13}$C NMR (125 MHz, CDCl$_3$) d (ppm): 159.2, 136.6, 130.8, 130.1, 129.3, 113.8, 83.2, 75.2, 73.4, 73.1, 69.5, 69.0, 55.4, 45.1, 44.2, 40.7, 33.2, 29.0, 26.1, 26.0, 21.8, 20.1, 18.2, 17.5, 7.1, 5.2, −3.9; [α]$_D^{20}$ 8.40 (c 0.66, chloroform).

Synthesis of Alkynyl Ester 21:

To a clear solution of alkyne (320.9 mg, 0.520 mmol) in THF (5 mL) at −78° C. was added n-BuLi (2.5 M HX, 250 mL, 0.625 mmol, 1.2 equiv) dropwise. After stirring 20 minutes, a neat solution of ethyl chloroformate (100 mL, 1.05 mmol, 2.0 equiv.) was added dropwise. The reaction was quenched with sat. NH$_4$Cl after 1 hr. and the flask was warmed to room temperature. The crude product was extracted with EA (×3), washed in brine, and dried over Na$_2$SO$_4$. Purification by flash chromatography (3% EA/HX) gave 347.7 mg (97% yield) of alkyne as a clear oil.

R$_f$=0.3 (5% EA/HX); $^1$H NMR (500 MHz, CDCl$_3$) d (ppm): 7.24 (d, J=8.7 Hz, 2H), 6.87 (d, J=8.6 Hz, 2H), 5.39 (dd, J=15.6, 8.2 Hz, 1H), 5.23 (dd, J=15.6, 7.6 Hz, 1H), 4.41 (d, J=11.5 Hz, 1H), 4.38 (d, J=11.5 Hz, 1H), 4.21 (q, J=7.2 Hz, 2H), 3.80 (s, 3H), 3.69-3.75 (m, 2H), 3.36 (dd, J=9.4, 5.4 Hz, 1H), 3.30 (dd, J=9.3, 6.0 Hz, 1H), 2.37 (dd, J=17.1, 5.0 Hz, 1H), 2.32 (dd, J=7.4, 3.4 Hz, 1H), 2.20-2.28 (m, 1H), 221 (dd, J=17.2, 7.3 Hz, 1H), 1.87 (m, 1H), 1.52 (m, 1H), 1.32-1.42 (m, 3H), 1.30 (t, J=7.2 Hz, 3H), 1.01 (d, J=7.1 Hz, 3H), 0.99 (d, J=7.4 Hz, 3H), 0.94 (t, J=8.2 Hz, 9H), 0.54-0.62 (m, 6H), 0.06 (S, 3H), 0.05 (s, 3H); $^{13}$C NMR (125 MHz, CDCl$_3$) d (ppm): 159.2, 153.9, 136.5, 130.8, 130.2, 129.3, 113.8, 88.2, 75.2, 74.5, 73.3, 73.1, 68.9, 61.9, 55.4, 44.9, 44.1, 40.7, 33.2, 28.7, 26.3, 26.1, 21.7, 20.3, 18.2, 17.5, 14.2, 7.1, 5.2, −3.9; [α]$_D^{20}$ 4.54 (c 0.91, chloroform).

Synthesis of Alkynyl Lactone 22:

To a clear solution of TES ether (346.6 mg, 0.503 mmol) in EtOH (5 mL) at 0° C. was added PPTS (25.4 mg, 0.101 mmol, 0.2 equiv.) in one portion. After 17 hrs., the reaction was quenched with sat. NaHCO$_3$ and flask warmed to room temperature. The crude product was extracted with EA (×3), washed in brine, and dried over Na$_2$SO$_4$.

To a clear solution of alkynyl ester in THF/H$_2$O (1:1, 5 mL) was added LiOH.H$_2$O (211.3 mg, 5.04 mmol, 10 equiv.) in one portion. After 18 hours, the reaction was quenched with 1 N HCl and the crude product was extracted with EA (×3), washed in brine, and dried over Na$_2$SO$_4$.

To a cloudy mixture of 2,4,6-trichlorobenzoyl chloride (105 mL, 0.672 mmol, 1.3 equiv.), DIPEA (440 mL, 2.53 mmol, 5.0 equiv.), and DMAP (30.9 mg, 0.253 mmol, 0.5 equiv.) in PhMe (90 mL) was added a clear solution of seco acid in PhMe (10 mL) slowly via cannula. After 2 hrs., the reaction was quenched with sat. NaHCO$_3$. The crude product was extracted with EA (×3), washed in brine, and dried over Na$_2$SO$_4$. Purification by flash chromatography (3% EA/HX) gave 178.4 mg (67% yield over 3-steps) of alkynyl lactone as a clear oil.

R$_f$=0.2 (5% EA/HX); $^1$H NMR (500 MHz, CDCl$_3$) d (ppm): 7.25 (d, J=8.6 Hz, 2H), 6.87 (d, J=8.6 Hz, 2H), 5.23 (dd, J=15.1, 9.4 Hz, 1H), 5.08 (dd, J=15.1, 9.6 Hz, 1H), 4.69 (ddd, J=10.5, 4.2, 2.6 Hz, 1H), 4.57 (d, J=11.9 Hz, 1H), 4.39 (d, J=11.9 Hz, 1H), 4.13 (m, 1H), 3.80 (s, 3H), 3.66 (dd, J=11.3, 2.6 Hz, 1H), 3.59 (dd, J=11.3, 4.3 Hz, 1H), 2.54-2.63 (m, 1H), 2.39 (dd, J=16.5, 3.2 Hz, 1H), 2.23-2.32 (m, 1H), 2.09-2.16 (m, 1H), 1.98 (dd, J=16.6, 10.7 Hz, 1H), 1.35-1.50 (m, 3H), 1.21-1.28 (m, 1H), 0.91-0.95 (m, 6H), 0.88 (s, 9H), 0.10 (s, 3H), 0.08 (s, 3H); $^{13}$C NMR (125 MHz, CDCl$_3$) d (ppm): 159.4, 153.5, 139.5, 130.9, 130.2, 129.5, 113.9, 90.4, 78.0, 75.3, 73.0, 71.0, 68.7, 55.4, 48.2, 47.9, 39.3, 34.8, 28.6, 27.0, 262, 24.0, 23.7, 18.5, 17.4, −2.9, −3.1; [α]$_D^{20}$ 1.65 (c 1.70, chloroform).

Synthesis of α,β-Unsaturated Lactone 23:

A black mixture of alkynyl lactone (68.0 mg, 0.129 mmol), quinoline (18 mL, 0.152 mmol, 1.2 equiv.), and Lindlar catalyst (14.1 mg) in EA/1-Hexene (1:1, 3 mL) was flushed with Ar (×5), H$_2$ (×5), and left vigorously stirring under an H$_2$ balloon. After 3 hrs., the reaction mixture was passed through celite and thoroughly rinsed with EA. Purification by flash chromatography (3% EA/HX) gave 67.4 mg (99% yield) of a,b-unsaturated lactone as a clear oil.

R$_f$=0.2 (5% EA/HX); $^1$H NMR (500 MHz, CDCl$_3$) d (ppm): 7.25 (d, J=8.4 Hz, 2H), 6.87 (d, J=8.7 Hz, 2H), 6.21 (td, J=12.1, 3.8 Hz, 1H), 5.92 (dd, J=11.7, 2.4 Hz, 1H) 5.16 (dd, J=15.2, 9.3 Hz, 1H), 5.03 (dd, J=15.1, 9.2 Hz, 1H), 4.95 (ddd, J=10.3, 4.5, 2.6 Hz, 1H), 4.56 (d, J=11.9 Hz, 1H), 4.40 (d, J=11.8 Hz, 1H), 3.81 (s, 3H), 3.69 (td, J=14.2, 4.6 Hz, 1H), 3.58 (dd, J=11.0, 4.6 Hz, 1H), 3.54 (dd, J=11.1, 2.6 Hz, 1H), 3.48 (t, J=9.9 Hz, 1H), 2.36-2.45 (m, 1H), 2.15-2.24 (m, 1H), 2.01-2.10 (m, 1H), 1.93 (dq, J=14.5, 32 Hz, 1H), 1.25-1.36 (m, 2H), 1.04 (dd, J=13.9, 11.2 Hz, 1H), 1.00 (d, J=7.0 Hz, 3H), 0.96 (d, J=6.9 Hz, 3H), 0.89 (d, J=6.9 Hz, 3H), 0.87 (s, 9H), 0.14 (s, 3H), 0.09 (s, 3H); $^{13}$C NMR (125 MHz, CDCl$_3$) d (ppm): 165.7, 159.3, 145.9, 137.6, 132.0, 130.3, 129.4, 122.2, 113.9, 74.6, 73.0, 69.7, 68.6, 55.4, 47.8, 44.9, 39.5, 34.7, 31.2, 27.6, 26.2, 22.9, 20.2, 18.5, 17.4, −3.0, −3.3; [α]$_D^{20}$ 40.6 (c 0.87, chloroform).

Synthesis of Carbamate 24:

HF.py (70%, 200 mL) was added dropwise to a clear solution of TBS ether (56.5 mg, 0.106 mmol) in MeOH (2 mL) at 0° C. in a plastic vial. After 4 hrs., the reaction was carefully quenched with sat. NaHCO$_3$ and the vial was warmed to room temperature. The crude product was extracted with EA (×3), washed in sat. NaHCO$_3$, brine, and dried over Na$_2$SO$_4$. Purification by flash chromatography (20% EA/HX) gave 41.8 mg of alcohol as a clear oil.

To a clear solution of alcohol (41.8 mg, 0.100 mmol) in DCM (2 mL) at 0° C. was added neat chlorosulfonyl isocyanate (11 mL, 0.126 mmol, 1.3 equiv.) dropwise. After 20 minutes, the reaction was slowly quenched with THF/H2O (4:1, 1 mL) and flask warmed to room temperature. Following 2 hrs. of vigorous stirring, the reaction was quenched with sat. NaHCO$_3$. The crude product was extracted with EA (×3), washed in brine, and dried over Na$_2$SO$_4$. Purification by flash chromatography (35% EA/HX) gave 392 mg (80% yield over 2-steps) of carbamate as a clear oil.

R$_f$=0.1 (35% EA/HX); $^1$H NMR (500 MHz, CDCl$_3$) d (ppm): 725 (d, J=9.1 Hz, 2H), 6.86 (d, J=8.7 Hz, 2H), 6.13 (td, J=12.0, 3.2 Hz, 1H), 5.95 (dd, J=11.6, 2.5 Hz, 1H), 5.32 (dd, J=15.1, 9.7 Hz, 1H), 4.99-5.06 (m, 2H), 4.51-4.60 (m, 3H), 4.39 (d, J=11.9 Hz, 1H), 3.80 (s, 3H), 3.71-3.79 (m, 1H), 3.54-3.61 (m, 2H), 2.41-2.50 (m, 1H), 2.04-2.13 (m, 1H), 1.96 (dq, J=15.0, 2.9 Hz, 1H), 1.84-1.92 (m, 1H), 1.46-1.54 (m, 2H), 1.02-1.09 (m, 1H), 1.01 (d, J=7.0 Hz, 3H), 0.94 (d, J=6.9 Hz, 3H), 0.91 (d, J=6.8 Hz, 3H); $^{13}$C NMR (125 MHz, CDCl$_3$) d (ppm): 165.4, 159.3, 156.8, 143.7, 136.4, 133.1, 130.3, 129.5, 122.8, 113.9, 74.6, 72.8, 71.4, 69.4, 55.4, 44.4, 41.4, 39.4, 34.0, 31.6, 27.4, 22.5, 20.3, 17.5; [α]$_D^{20}$ 14.1 (c 0.85, chloroform).

Synthesis of Vinyl Iodide 2:

To a clear/yellow biphasic mixture of PMB ether (36.0 mg, 0.078 mmol) in DCM/pH 7.0 phosphate buffer (1:1, 1.5 mL) was added DDQ (39.0 mg, 0.172 mmol, 2.2 equiv.). After 1 hr., additional DDQ was added (17.0 mg, 0.075 mmol, 1.0 equiv.). The reaction was quenched following 3 hrs. and crude product extracted with EA (×3), washed in sat. NaHCO$_3$, brine, and dried over Na$_2$SO$_4$. Purification by flash chromatography (75% EA/HX) gave 20.8 mg of alcohol as a clear oil.

To a clear solution of alcohol (20.8 mg, 0.061 mmol) in DCM (2 mL) at 0° C. was added NaHCO$_3$ (25.7 mg, 0.306 mmol, 5.0 equiv.) and DMP (51.7 mg, 0.122 mmol, 2.0 equiv.) sequentially. The ice bath was removed after addition, reaction left stirring 1.5 hrs., then quenched with 3 mL sat. Na$_2$S$_2$O$_3$/sat. NaHCO$_3$ (1:1). The crude product was extracted with EA (×3), washed in brine, and dried over Na₂SO₄. Purification through a short silica plug (50% EA/HX) gave 13.6 mg of aldehyde as a white solid.

A yellow solution of aldehyde (13.6 mg, 0.040 mmol) and CHI₃ (47.2 mg, 0.120 mmol, 3.0 equiv.) in THF (1 mL) was added via cannula to a green suspension of CrCl₂ (49.3 mg, 0.401 mmol, 10.0 equiv.) in THF (1 mL). After 2 hrs., the reaction was quenched with H₂O and crude product extracted with EA (×3), washed in brine, and dried over Na₂SO₄. Purification through a short silica plug (40% EA/HX) gave 15.2 mg (42% yield over 3-steps) of vinyl iodide as a white solid.

$R_f$=0.2 (25% EA/HX); ¹H NMR (500 MHz, CDCl₃) d (ppm): 6.43-6.53 (m, 2H), 6.13 (td, J=12.3, 3.4 Hz, 1H), 5.87 (dd, J=11.5, 2.5 Hz, 1H), 5.82 (dd, J=15.1, 9.5 Hz, 1H), 5.19 (ddd, J=10.3, 5.6, 2.0 Hz, 1H), 5.04 (dd, J=15.0, 9.3 Hz, 1H), 4.58 (t, J=11.0 Hz, 1H), 4.46 (brs, 2H), 3.67 (ddd, J=15.0, 12.9, 5.0 Hz, 1H), 2.18-2.27 (m, 1H), 2.05-2.13 (m, 1H), 1.96 (dq, J=15.0, 2.7 Hz, 1H), 1.84-1.92 (m, 1H), 1.45-1.53 (m, 2H), 1.03-1.11 (m, 1H), 1.01 (d, J=7.0 Hz, 3H), 0.95 (d, J=6.8 Hz, 3H), 0.92 (d, J=6.8 Hz, 3H); further spectroscopic data was not collected due to concern of decomposition.

Synthesis of Alcohol 8:

To a grey mixture of phenol (2.0692 g, 10.3 mmol) in DCM (50 mL) at 0° C. was added DIPEA (3.5 mL, 20.1 mmol, 2.0 equiv.) and TBSCl (1.9755 g, 13.1 mmol, 1.3 equiv.) sequentially. After 4 hrs., the yellow solution was quenched with sat. NH₄Cl. The crude product was extracted with EA (×3), washed in brine, and dried over Na₂SO₄. Purification by flash chromatography (3% EA/HX) gave 3.1808 g of TBS phenol as a clear oil.

To a clear solution of aldehyde (2.0692 g, 6.6 mmol) in THF (35 mL) at 0° C. was added a grey solution of 3-methyl-2-butenylmagnesium chloride (1 M THF, 8.0 mL, 8.0 mmol, 1.2 equiv.) slowly. After 30 minutes, the reaction was quenched with sat. NH₄Cl. The crude product was extracted with EA (×3), washed in brine, and dried over Na₂SO₄. Purification by flash chromatography (3% EA/HX) gave 3.8880 g (98% yield over 2-steps) of alcohol as a clear oil.

$R_f$=0.3 (5% EA/HX); ¹H NMR (500 MHz, CDCl₃) d (ppm): 7.15 (t, J=7.9 Hz, 1H), 7.08 (dd, J=7.8, 1.6 Hz, 1H), 6.81 (dd, J=7.9, 1.6 Hz, 1H), 6.03 (dd, J=17.6, 10.8 Hz, 1H), 5.15 (s, 1H), 5.14 (dd, J=10.8, 1.3 Hz, 1H), 5.07 (dd, J=17.5, 1.3 Hz, 1H), 1.99 (s, 1H), 1.12 (s, 3H), 1.05 (s, 9H), 1.04 (s, 3H), 0.25 (s, 3H), 0.23 (s, 3H); ¹³C NMR (125 MHz, CDCl₃) d (ppm): 152.3, 144.9, 142.4, 127.0, 122.2, 119.1, 118.2, 114.0, 78.0, 43.6, 26.0, 24.8, 21.5, 18.6, -4.0, -4.1.

Synthesis of Alcohol (S)-8:

To a cloudy suspension of alcohol (2.4435 g, 6.34 mmol) and SiO₂ (2.8888 g) in DCM (32 mL) was added PCC (2.0503 g, 9.51 mmol, 1.5 equiv.) portionwise. After 12 hrs., the reaction was filtered through celite and the filter cake was washed with DCM. Purification by flash chromatography (3% EA/HX) gave 2.2594 g of ketone as a clear oil.

To a faint-yellow solution of ketone (2.2594 g, 5.89 mmol) and (S)-Me-CBS (1.6325 g, 5.89 mmol, 1.0 equiv.) in PhMe (60 mL) at 0° C. was added BMS (1.1 mL, 11.6 mmol, 2.0 equiv.) dropwise. After 2 hrs., the reaction was quenched with MeOH dropwise, flask warmed to room temperature, and concentrated via rotary evaporation. Purification by flash chromatography (3% EA/HX) gave 1.2955 g (53% yield over 2-steps) of alcohol as a clear oil.

$[\alpha]_D^{20}$-50.8 (c 1.85, chloroform). Chiral HPLC: Chiralpak IC3 (250×4.6 mm), 5% IPA/HX, flow=0.5 mL/min, T=20° C., UV=254 nm, $R_t$ major=7.9 min, $R_t$ minor=9.2 min.

Synthesis of Alcohol (R)-8:

Prepared in the same manner as alcohol (S)-8 above employing (R)-Me-CBS catalyst. $[\alpha]_D^{20}$-49.2 (c 2.13, chloroform).

Synthesis of Benzoate (S)-27:

To a clear solution of alcohol (32.0 mg, 0.083 mmol) in DCM (2 mL) was added Et₃N (35 mL, 0251 mmol, 3.0 equiv.), 4-nitrobenzoyl chloride (24.5 mg, 0.132 mmol, 1.6 equiv.), and DMAP (2.0 mg, 0.016 mmol, 0.2 equiv.) sequentially. After 3 hrs., the reaction was quenched with sat. NaHCO₃. The crude product was extracted with DCM (×3), washed in brine, and dried over MgSO₄. Purification by flash chromatography (3% EA/HX) gave 42.6 mg (96% yield) of benzoate as an opaque solid.

$R_f$=0.4 (5% EA/HX); ¹H NMR (500 MHz, CDCl₃) d (ppm): 8.29 (d, J=9.0 Hz, 2H), 8.22 (d, J=9.0 Hz, 2H), 7.11 (t, J=7.9 Hz, 1H), 7.01 (dd, J=7.8, 1.5 Hz, 1H), 6.82 (dd, J=8.0, 1.6 Hz, 1H), 6.45 (s, 1H), 6.09 (dd, J=17.4, 10.8 Hz, 1H), 5.11 (dd, J=10.8, 1.1 Hz, 1H), 5.05 (dd, J=17.4, 1.1 Hz, 1H), 1.22 (s, 3H), 1.19 (s, 3H), 1.05 (s, 9H), 0.26 (s, 3H), 0.25 (s, 3H); ¹³C NMR (125 MHz, CDCl₃) d (ppm): 163.6, 152.6, 150.7, 143.4, 138.9, 135.9, 130.8, 127.1, 123.7, 121.6, 119.4, 118.7, 113.9, 81.4, 42.5, 25.9, 24.6, 22.6, 18.5, -4.1; $[\alpha]_D^{20}$ 170.5 (c 1.77, chloroform).

Synthesis of TES Ether (S)-25:

To a clear solution of alcohol (153.7 mg, 0.399 mmol) in DCM (3 mL) at 0° C. was added Et₃N (170 mL, 1.22 mmol, 3.1 equiv.) and TESOTf (135 mL, 0.597 mmol, 1.5 equiv.) sequentially. After 30 minutes, the reaction was quenched with sat. NaHCO₃ and flask warmed to room temperature. The crude product was extracted with DCM (×3), washed in brine, and dried over MgSO₄. Purification by flash chromatography (2% EA/HX) gave 191.3 mg (96% yield) of TES ether as a clear oil.

$R_f$=0.7 (5% EA/HX); ¹H NMR (500 MHz, CDCl₃) d (ppm): 7.09 (t, J=4.8 Hz, 2H), 6.78 (quint, J=4.7, 1H), 6.08 (dd, J=17.7, 10.9 Hz, 1H), 5.06 (s, 1H), 4.94 (dd, J=10.8, 1.3 Hz, 1H), 4.84 (dd, J=17.6, 1.3 Hz, 1H), 1.07 (s, 3H), 1.05 (s, 9H), 1.00 (s, 3H), 0.83 (t, J=8.2 Hz, 9H), 0.22 (s, 3H), 0.21 (s, 3H); ¹³C NMR (125 MHz, CDCl₃) d (ppm): 181.8, 145.1, 143.9, 126.5, 123.5, 119.0, 117.9, 112.0, 79.1, 43.8, 26.1, 24.3, 22.6, 18.6, 6.9, 4.9, -4.0, -4.1; $[\alpha]_D^{20}$-18.64 (c 1.03, chloroform).

Synthesis of TES Ether (R)-25:

Prepared in the same manner as TES ether (S)-25 above. $[\alpha]_D^{20}$ 17.69 (c 1.45, chloroform).

Synthesis of Enzyne (S)-3:

To a clear solution of olefin (238.9 mg, 0.478 mmol) in acetone/H₂O (5 mL) was added 2,6-lutidine (110 mL, 0.944 mmol, 2.0 equiv.), NMO (115.2 mg, 0.983 mmol, 2.1 equiv.), and OsO₄ (4% in H₂O, 0.6 mL, 0.094 mmol, 0.2 equiv.) sequentially. The yellow solution was left stirring overnight while covered with aluminum foil. After 12 hrs., PhI(OAc)₂ (240.2 mg, 0.746 mmol, 1.6 equiv.) was added and reaction left stirring additional 30 minutes. The reaction was quenched with Na₂S₂O₃ and left vigorously stirring 15 minutes. The crude product was extracted with EA (×3), washed in brine, and dried over Na₂SO₄. Purification by flash chromatography (3% EA/HX) gave 224.0 mg of aldehyde as a clear oil.

To a cream-colored suspension of phosphonium bromide (822.0 mg, 1.81 mmol, 4.0 equiv.) in THF (10 mL) at -78° C. was added LHMDS (1 M THF, 1.8 mL, 1.80 mmol, 4.0 equiv.) slowly. After 10 minutes, the flask was warmed to -40° C. for an additional 30 minutes, then recooled to -78° C. A clear solution of aldehyde (224.0 mg, 0.447 mmol) in THF (5 mL) was then added slowly via cannula. The flask was then slowly warmed to room temperature and left stirring overnight. After 12 hrs., the reaction was quenched with sat. NH$_4$Cl. The crude product was extracted with EA (×3), washed in brine, and dried over Na$_2$SO$_4$. Purification by flash chromatography (3% EA/HX) gave 272.2 mg of TMS-enyne as a clear oil with a 7:1 trans/ds ratio as determined by $^1$H NMR.

To a clear solution of tri-silyl ether (272.2 mg, 0.478 mmol) in THF (5 mL) was added TBAF (1 M THF, 2.4 mL, 2.40 mmol, 5.0 equiv.) slowly. After 20 hrs., the reaction was quenched with sat. NH$_4$Cl. The crude product was extracted with EA (×3), washed in brine, and dried over Na$_2$SO$_4$. Purification by flash chromatography (15% EA/HX) gave 72.0 mg (51% yield over 3-steps) of enyne as a clear oil.

R$_f$=0.2 (15% EA/HX); $^1$H NMR (500 MHz, CDCl$_3$) d (ppm): 7.23 (t, J=8.0 Hz, 1H), 7.03 (dd, J=7.8, 1.1 Hz, 1H), 6.97 (dd, J=8.0, 1.1 Hz, 1H), 6.45 (d, J=16.4, 1H), 5.69 (s, 1H), 5.42 (dd, J=16.4, 2.2 Hz, 1H), 5.00 (s, 1H), 2.85 (d, J=2.2 Hz, 1H), 1.97 (s, 1H), 1.14 (s, 3H), 1.05 (s, 3H); $^{13}$C NMR (125 MHz, CDCl$_3$) d (ppm): 151.9, 151.6, 141.1, 1282, 121.4, 115.3, 112.8, 108.1, 78.5, 77.0, 43.6, 24.3, 21.9; [α]$_D^{20}$ –98.47 (c 0.33, chloroform).

Synthesis of Enyne (R)-3:
Prepared in the same manner as TES ether (S)-3 above. [α]$_D^{20}$ 100.6 (c 0.867, chloroform).

Synthesis of Dienyne (S)-1:
To a clear solution of vinyl iodide (8.6 mg, 0.019 mmol) and enyne (8.4 mg, 0.028 mmol, 1.5 equiv.) in degassed PhMe (3 mL) was added pyrrolidine (3 mL, 0.036 mmol, 1.9 equiv.) and CuI (0.7 mg, 0.004 mmol, 0.2 equiv.) sequentially to give a faint-red solution. After stirring 5 minutes, Pd(PPh$_3$)$_4$ (2.2 mg, 0.002 mmol, 0.1 equiv.) was added to produce a faint-yellow solution. Following 45 minutes, the reaction was passed through a short plug of silica and eluted with Et$_2$O. Purification by flash chromatography (25% EA/HX) gave 9.2 mg (79% yield over 3-steps) of callyspongiolide, (S)-1 as a clear oil.

R$_f$=0.14 (40% EA/HX); $^1$H NMR (500 MHz, DMSO-ds) d (ppm): 10.06 (brs, 1H), 7.13 (t, J=7.8 Hz, 1H), 6.81-6.85 (m, 2H), 6.36 (d, J=16.4 Hz, 1H), 6.13 (td, J=12.0, 3.2 Hz, 1H), 6.06 (dd, J=15.8, 7.7 Hz, 1H), 5.91-5.97 (m, 2H), 5.52 (d, J=4.4 Hz, 1H), 5.46 (dd, J=16.4, 1.9 Hz, 1H), 522 (dd, J=15.0, 9.4 Hz, 1H), 5.09 (dd, J=10.1, 8.0 Hz, 1H), 5.05 (dd, J=15.0, 9.0 Hz, 1H), 4.89 (d, J=4.4 Hz, 1H), 4.47 (t, J=10.8 Hz, 1H), 3.42 (app td, J=15.2, 4.9 Hz, 1H), 2.19-2.28 (m, 1H), 1.95-2.04 (m, 1H), 1.86 (dd, J=15.0, 2.2 Hz, 1H), 1.69-1.79 (m, 1H), 1.33-1.44 (m, 2H), 1.00-1.07 (m, 5H), 0.94-0.99 (m, 6H), 0.88 (t, J=6.9 Hz, 6H); $^{13}$C NMR (125 MHz, DMSO-ds) d (ppm): 164.2, 156.7, 153.3, 151.6, 143.2, 142.5, 139.6, 136.4, 132.0, 126.9, 122.3, 120.1, 114.3, 113.4, 111.7, 106.8, 90.4, 86.4, 76.6, 75.7, 68.3, 44.1, 43.1, 41.8, 41.1, 33.3, 31.3, 26.9, 24.1, 22.4, 22.0, 19.9, 17.5; [α]$_D^{20}$ 51.50 (c 0.468, chloroform).

Synthesis of Dienyne (R)-1:
To a clear solution of vinyl iodide (3.2 mg, 0.007 mmol) and enyne (3.1 mg, 0.011 mmol, 1.6 equiv.) in degassed PhMe (2 mL) was added pyrrolidine (1.5 mL, 0.018 mmol, 2.6 equiv.) and CuI (0.7 mg, 0.004 mmol, 0.6 equiv.) sequentially to give a faint-red solution. After stirring 5 minutes, Pd(PPh$_3$)$_4$ (0.9 mg, 0.001 mmol, 0.1 equiv.) was added to produce a faint-yellow solution. Following 45 minutes, the reaction was passed through a short plug of silica and eluted with Et$_2$O. Purification by flash chromatography (25% EA/HX) gave 3.6 mg (82% yield) of callyspongiolide, (R)-1 as a clear oil.

R$_f$=0.14 (40% EA/HX); $^1$H NMR (500 MHz, DMSO-ds) d (ppm): 10.12 (brs, 1H), 7.12 (t, J=7.8 Hz, 1H), 6.83 (d, J=7.8 Hz, 2H), 6.36 (d, J=16.3 Hz, 1H), 6.13 (td, J=122, 3.3 Hz, 1H), 6.06 (dd, J=15.8, 7.7 Hz, 1H), 5.91-5.97 (m, 2H), 5.51 (d, J=4.2 Hz, 1H), 5.45 (dd, J=16.4, 1.9 Hz, 1H), 522 (dd, J=15.0, 9.3 Hz, 1H), 5.09 (dd, J=10.1, 7.8 Hz, 1H), 5.05 (dd, J=14.9, 9.0 Hz, 1H), 4.89 (d, J=3.9 Hz, 1H), 4.47 (t, J=10.9 Hz, 1H), 3.42 (app td, J=15.0, 4.9 Hz, 1H), 2.19-2.28 (m, 1H), 1.95-2.04 (m, 1H), 1.86 (dd, J=14.8, 22 Hz, 1H), 1.69-1.79 (m, 1H), 1.33-1.44 (m, 2H), 1.00-1.07 (m, 5H), 0.94-0.99 (m, 6H), 0.88 (t, J=6.9 Hz, 6H); $^{13}$C NMR (125 MHz, DMSO-ds) d (ppm): 164.2, 156.7, 153.4, 151.7, 143.2, 142.5, 139.6, 136.4, 132.0, 126.9, 122.3, 120.0, 114.4, 113.4, 111.7, 106.8, 90.4, 86.4, 76.6, 75.7, 68.3, 44.1, 43.1, 41.8, 41.1, 33.3, 31.3, 26.9, 24.1, 22.5, 22.0, 19.9, 17.5; [α]$_D^{20}$ 209.0 (c 0255, chloroform).

The present invention provides for the following examples, the numbering of which is not to be construed as designating levels of importance:

Example 1 relates to a method of making a compound of the formula (III):

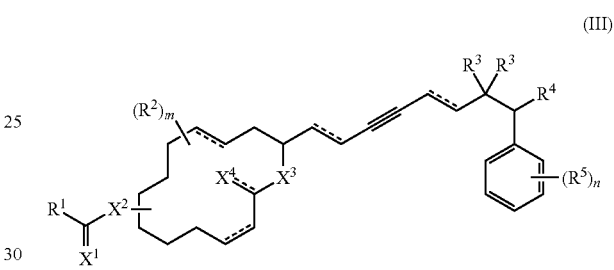

(III)

or a pharmaceutically acceptable salt, polymorph, prodrug, solvate or clathrate thereof; comprising:
contacting a compound of the formula (IV):

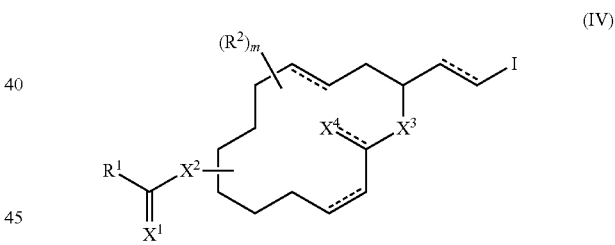

(IV)

with a compound of the formula (V):

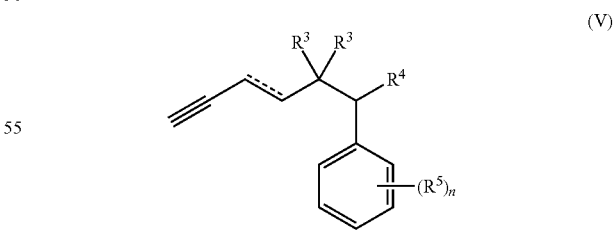

(V)

wherein:
each dashed bond independently represents a single or a double bond and, when a dashed bond represents a double bond, the double bond can have the E- or Z-configuration;
R$^1$ is H, alkyl, R$^2$—(CH$_2$)$_q$—X$^3$—, R$^2$—(CH$_2$)$_q$—C(O)NR$^6$(CH$_2$)$_q$—X$^3$—, OR$^6$ or N(R$^6$)$_2$, wherein each R$^6$ independently represents H, alkyl, aryl, alkaryl, or arylalkyl and each q is, independently an integer from 0 to 9; $X^1$ is O, $NR^6$ or S; $X^2$ is O, $NR^6$ or S; each $R^2$ is, independently, H, halo, alkyl, aryl, alkaryl, arylalkyl, heterocyclyl, $OR^6$, $S(O)_pR^6$ or $N(R^6)_2$, wherein p is an integer from 0 to 2 and m is an integer from 1 to 10; $X^3$ is O, $NR^6$, $S(O)_p$ or $C(R^6)_2$; $X^4$ is O, $NR^6$ or S or $X^4$ is $R^2$ when there is a single bond between $X^4$ and the carbon atom to which $X^4$ is bound; each $R^3$ is, independently, H, halo, alkyl, aryl, alkaryl, arylalkyl, heterocyclyl, $OR^6$, $S(O)_pR^6$ or $N(R^6)_2$; $R^4$ is H, halo, alkyl, aryl, alkaryl, arylalkyl, heterocyclyl, $OR^6$, $S(O)_pR^6$, $N(R^6)_2$ or $X^1C(O)(CH)_qR^6$; and each $R^5$ is, independently, H, halo, alkyl, aryl, alkaryl, arylalkyl, heterocyclyl, $OR^6$, $S(O)_pR^6$ or $N(R^6)_2$, wherein n is an integer from 0 to 4.

Example 2 relates to the method of Example 1, wherein m is 3 and/or n is 2.

Example 3 relates to the method of Examples 1-2, wherein the compound of the formula (IV) is a compound of the formula (X):

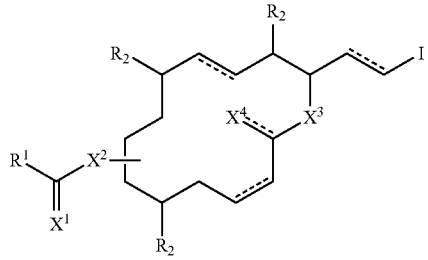

(X)

such that the compound of the formula (III) is a compound of the formula:

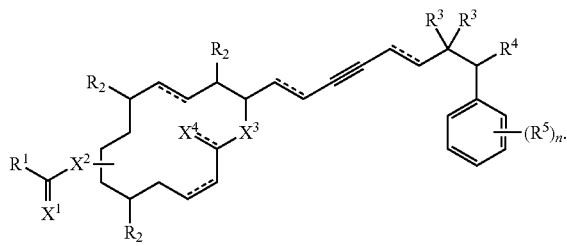

Example 4 relates to the method of Example 1, wherein the compound of the formula (V) is a compound of the formula (XI):

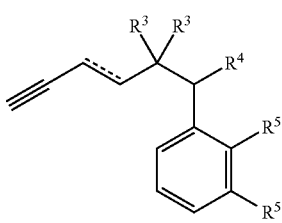

(XI)

such that the compound of the formula (III) is a compound of the formula:

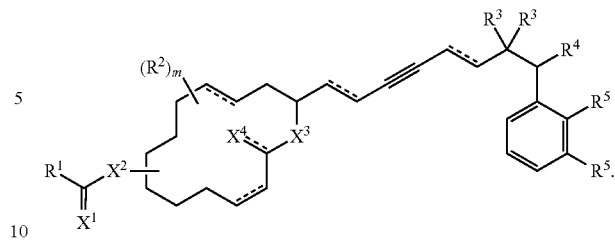

Example 5 relates to the method of Example 1, wherein the compound of the formula (III) is a compound of the formula:

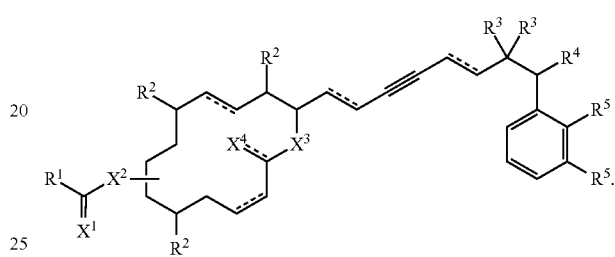

Example 6 relates to the method of Example 1, wherein the compound of formula (III) is a compound of the formula:

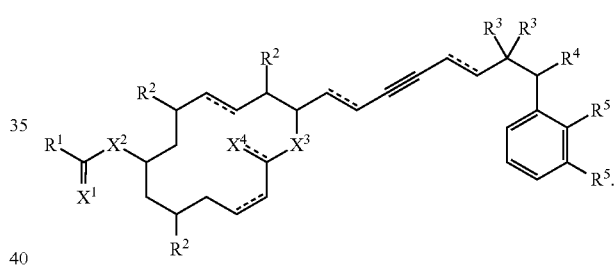

Example 7 relates to the method of Example 1, wherein the compound of formula (III) is a compound of formula:

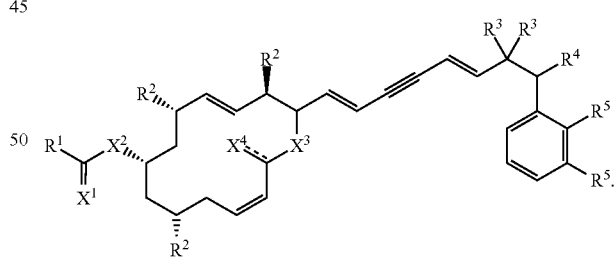

Example 8 relates to the method of Examples 1-7, wherein $X^1$, $X^2$, $X^3$ and $X^4$ are each O.

Example 9 relates to the method of Examples 1-8, wherein each dashed bond represents a double bond in the configuration shown.

Example 10 relates to the method of Examples 1-9, wherein $R^1$ is $N(R^6)_2$, wherein each $R^6$ independently represents H, alkyl, aryl, alkaryl, or arylalkyl.

Example 11 relates to the method of Examples 1-10, wherein each $R^2$ is, independently, $C_1$-$C_6$ alkyl.

Example 12 relates to the method of Examples 1-11, wherein each $R^5$ is, independently, halo or $OR^6$.

Example 13 relates to the method of Examples 1-12, wherein each $R^3$ is, independently, $C_1$-$C_6$ alkyl.

Example 14 relates to the method of Examples 1-13, wherein $R^4$ is $OR^6$.

Example 15 relates to the method of Examples 1-14, wherein the compound of the formula (III) is a compound of the formula (I):

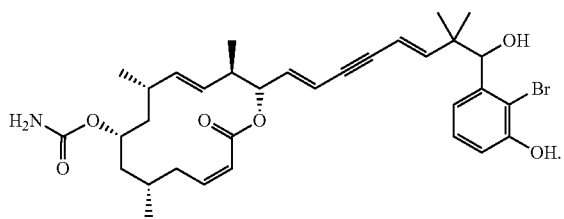

(I)

Example 16 relates to a compound of the formula (III):

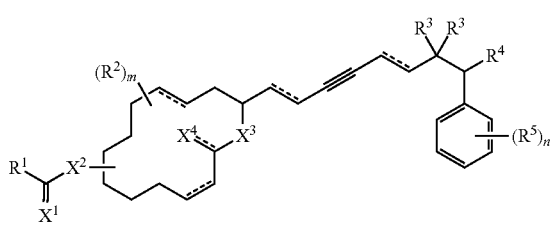

(III)

or a pharmaceutically acceptable salt, polymorph, prodrug, solvate or clathrate thereof; wherein: each dashed bond independently represents a single or a double bond and, when a dashed bond represents a double bond, the double bond can have the E- or Z-configuration; $R^1$ is H, alkyl, $R^2$—$(CH_2)_q$—$X^3$—, $R^2$—$(CH_2)_q$—$C(O)NR^6(CH_2)_q$—$X^3$—, $OR^6$ or $N(R^6)_2$, wherein each $R^6$ independently represents H, alkyl, aryl, alkaryl, or arylalkyl and each q is, independently an integer from 0 to 9; $X^1$ is O, $NR^6$ or S; $X^2$ is O, $NR^6$ or S; each $R^2$ is, independently, H, halo, alkyl, aryl, alkaryl, arylalkyl, heterocyclyl, $OR^6$, $S(O)_pR^6$ or $N(R^6)_2$, wherein p is an integer from 0 to 2 and m is an integer from 1 to 10; $X^3$ is O, $NR^6$, $S(O)_p$ or $C(R^6)_2$; $X^4$ is O, $NR^6$ or S or $X^4$ is $R^2$ when there is a single bond between $X^4$ and the carbon atom to which $X^4$ is bound; each $R^3$ is, independently, H, halo, alkyl, aryl, alkaryl, arylalkyl, heterocyclyl, $OR^6$, $S(O)_pR^6$ or $N(R^6)_2$; $R^4$ is H, halo, alkyl, aryl, alkaryl, arylalkyl, heterocyclyl, $OR^6$, $S(O)_pR^6$, $N(R^6)_2$ or $X^1C(O)(CH)_qR^6$; and each $R^5$ is, independently, H, halo, alkyl, aryl, alkaryl, arylalkyl, heterocyclyl, $OR^6$, $S(O)_pR^6$ or $N(R^6)_2$, wherein n is an integer from 0 to 4; and wherein the compound of the formula (III) is not a compound of the formula (I) or (II):

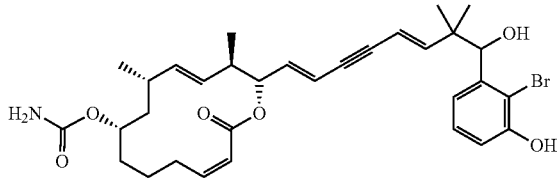

(I)

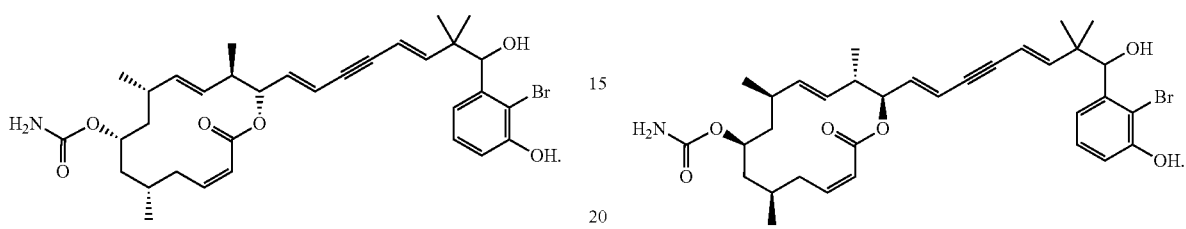

(II)

Example 17 relates to a pharmaceutical composition comprising a compound of Example 16 and pharmaceutically acceptable carrier.

Example 18 relates to a method for treating cancer comprising administering a therapeutically effective amount one or more compounds of Example 16 or a pharmaceutical composition comprising one or more compounds of Example 16 to a subject in need thereof.

Example 19 relates to a compound of Example 16 for use as a medicament for treating a patient in need of relief from cancer.

What is claimed is:

1. A compound of the formula (III):

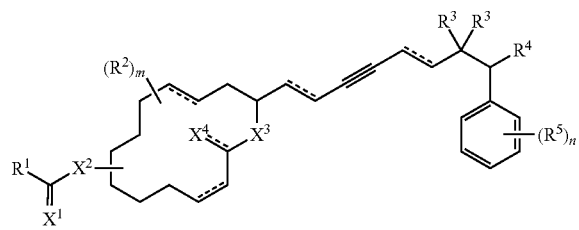

or a pharmaceutically acceptable salt, polymorph, solvate or clathrate thereof wherein:
each dashed bond independently represents a single or a double bond and, when a dashed bond represents a double bond, the double bond can have the E- or Z-configuration;
$R^1$ is H, alkyl, $R^2$—$(CH_2)_q$—$X^3$—, $R^2$—$(CH_2)_q$—$C(O)NR^6(CH_2)_q$—$X^3$—, $OR^6$ or $N(R^6)_2$, wherein each $R^6$ independently represents H, alkyl, aryl, alkaryl, or arylalkyl and each q is, independently an integer from 0 to 9;
$X^1$ is O, $NR^6$ or S;
$X^2$ is O, $NR^6$ or S;
each $R^2$ is, independently, H, halo, alkyl, aryl, alkaryl, arylalkyl, heterocyclyl, $OR^6$, $S(O)_pR^6$ or $N(R^6)_2$, wherein p is an integer from 0 to 2 and m is an integer from 1 to 10;
$X^3$ is O, $NR^6$, $S(O)_p$ or $C(R^6)_2$;
$X^4$ is O, $NR^6$ or S or $X^4$ is $R^2$ when there is a single bond between $X^4$ and the carbon atom to which $X^4$ is bound;

each $R^3$ is, independently, H, halo, alkyl, aryl, alkaryl, arylalkyl, heterocyclyl, $OR^6$, $S(O)_pR^6$ or $N(R^6)_2$;

$R^4$ is H, halo, alkyl, aryl, alkaryl, arylalkyl, heterocyclyl, $OR^6$, $S(O)_pR^6$, $N(R^6)_2$ or $X^1C(O)(CH)_qR^6$; and each $R^5$ is, independently, H, halo, alkyl, aryl, alkaryl, arylalkyl, heterocyclyl, $OR^6$, $S(O)_pR^6$ or $N(R^6)_2$, wherein n is an integer from 0 to 4; and wherein the compound of the formula (III) is not a compound of the formula (I) or (II):

(I)
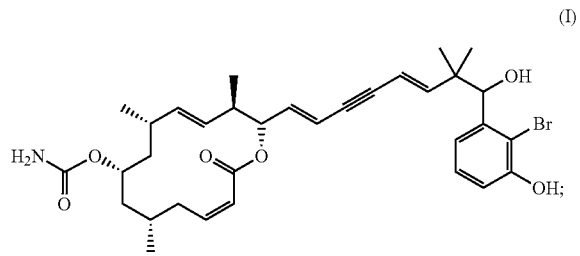

(II)
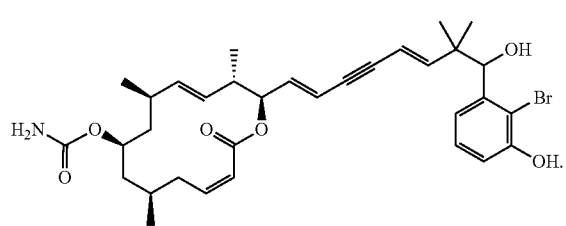

2. The compound of claim 1, wherein m is 3.

3. The compound of claim 1, wherein n is 2.

4. The compound of claim 1, wherein the compound of formula (III) is a compound of the formula:

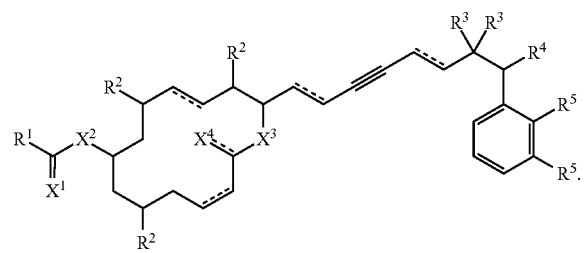

5. The compound of claim 1, wherein the compound of formula (III) is a compound of formula:

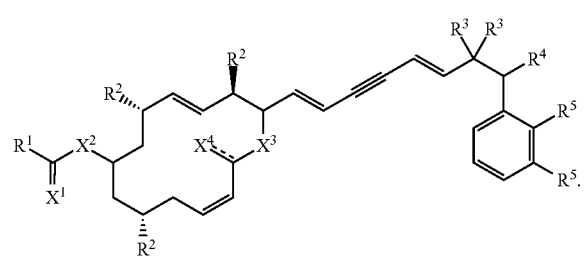

6. The compound of claim 1, wherein $X^1$, $X^2$, $X^3$ and $X^4$ are each O.

7. The compound of claim 1, wherein $R^1$ is $N(R^6)_2$, wherein each $R^6$ independently represents H, alkyl, aryl, alkaryl, or arylalkyl.

8. The compound of claim 1, wherein each $R^2$ is, independently, $C_1$-$C_6$ alkyl.

9. The compound of claim 1, wherein each R is, independently, halo or $OR^6$.

10. The compound of claim 1, wherein each $R^3$ is, independently, $C_1$-$C_6$ alkyl.

11. The compound of claim 1, wherein $R^4$ is $OR^6$.

12. A compound of the formula:

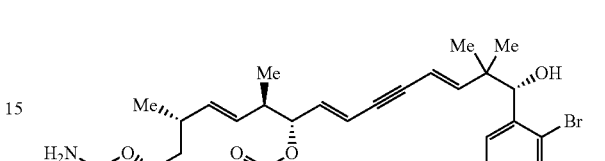

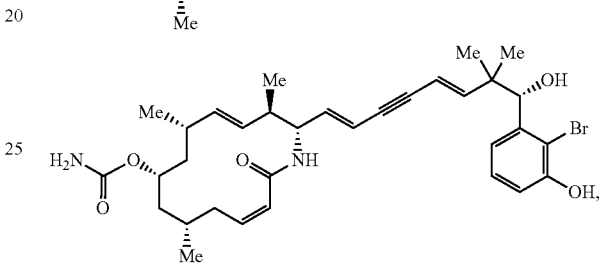

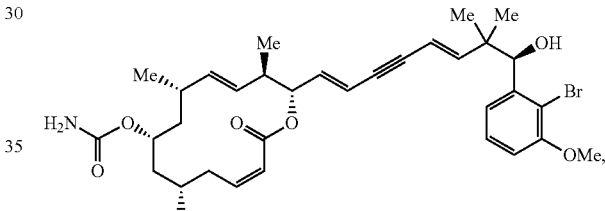

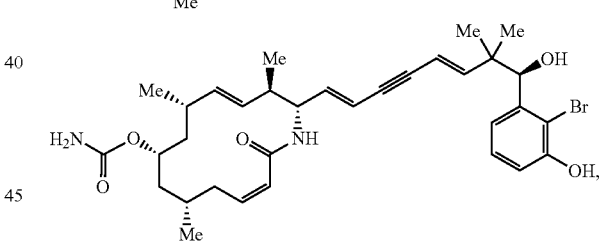

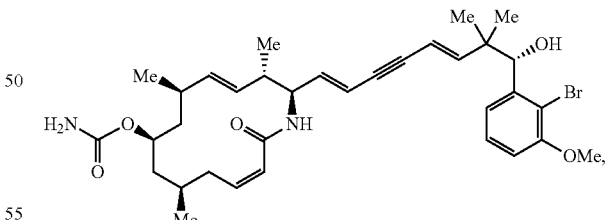

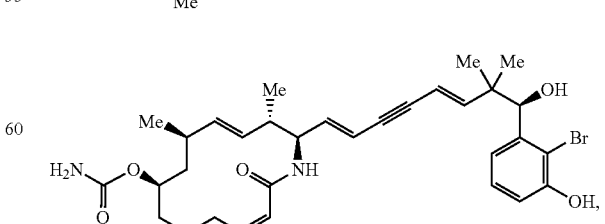

or a pharmaceutically acceptable salt, polymorph, solvate or clathrate thereof.

13. A pharmaceutical composition comprising a compound of claim and a pharmaceutically acceptable carrier.

14. A method for treating cancer comprising administering a therapeutically effective amount of one or more compounds of claim 1 to a subject in need thereof.

15. A method of making a compound of the formula (III):

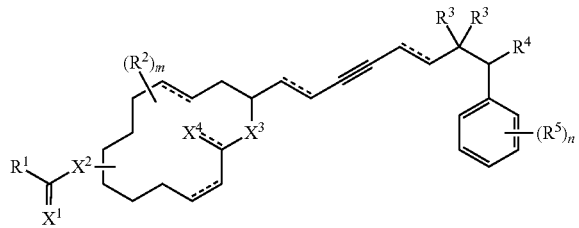

or a pharmaceutically acceptable salt, polymorph, solvate or clathrate thereof;

comprising:

contacting a compound of the formula (IV):

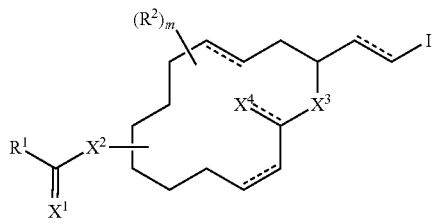

with a compound of the formula (V):

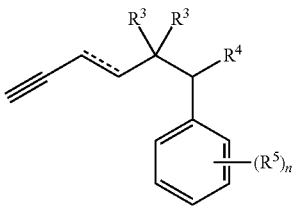

wherein:

each dashed bond independently represents a single or a double bond and, when a dashed bond represents a double bond, the double bond can have the E- or Z-configuration;

$R^1$ is H alkyl, $R^2-(CH_2)_q-X^3-$, $R^2-(CH_2)_q-C(O)NR^6(CH_2)_q-X^3-$, $OR^6$ or $N(R^6)_2$, wherein each $R^6$ independently represents H, alkyl, aryl, alkaryl, or arylalkyl and each q is, independently an integer from 0 to 9;

$X^1$ is O, $NR^6$ or S;

$X^2$ is O, $NR^6$ or S;

each $R^2$ is, independently, H, halo, alkyl, aryl, alkaryl, arylalkyl, heterocyclyl, $OR^6$, $S(O)_pR^6$ or $N(R^6)_2$, wherein p is an integer from 0 to 2 and m is an integer from 1 to 10;

$X^3$ is O, $NR^6$, S(O), or $C(R^6)_2$;

$X^4$ is O, $NR^6$ or S or $X^4$ is $R^2$ when there is a single bond between $X^4$ and the carbon atom to which $X^4$ is bound;

each $R^3$ is, independently, H, halo, alkyl, aryl, alkaryl, arylalkyl, heterocyclyl, $OR^6$, $S(O)R^6$ or $N(R^6)_2$;

$R^4$ is H, halo, alkyl, aryl, alkaryl, arylalkyl, heterocyclyl, $OR^6$, $S(O),R^6$, $N(R^6)_2$ or $X^1C(O)(CH)R^6$; and each $R^5$ is, independently, H, halo, alkyl, aryl, alkaryl, arylalkyl, heterocyclyl, $OR^6$, $S(O)_pR^6$ or $N(R^6)_2$, wherein n is an integer from 0 to 4.

* * * * *